US008917916B2

(12) United States Patent
Martin et al.

(10) Patent No.: US 8,917,916 B2
(45) Date of Patent: Dec. 23, 2014

(54) MEDICAL TRAINING METHOD AND APPARATUS

(76) Inventors: Colin Bruce Martin, Gerrards Cross (GB); Susan Jane Wright, London (GB); Andrew Smith, High Barnet (GB); Adam William Jon Cubitt, London (GB)

( * ) Notice: Subject to any disclaimer, the term of this patent is extended or adjusted under 35 U.S.C. 154(b) by 1043 days.

(21) Appl. No.: 12/919,003

(22) PCT Filed: Feb. 25, 2008

(86) PCT No.: PCT/GB2008/000636
§ 371 (c)(1), (2), (4) Date: Mar. 25, 2011

(87) PCT Pub. No.: WO2009/106784
PCT Pub. Date: Sep. 3, 2009

(65) Prior Publication Data

US 2011/0170752 A1 Jul. 14, 2011

(51) Int. Cl.
*G06K 9/00* (2006.01)
*G09B 23/28* (2006.01)

(52) U.S. Cl.
CPC .................................... *G09B 23/285* (2013.01)
USPC ............................ 382/128; 600/437; 434/267

(58) Field of Classification Search
USPC ............................ 382/128; 600/437; 434/267
See application file for complete search history.

(56) References Cited

U.S. PATENT DOCUMENTS 6,766,062 B1 * 7/2004 Donoho et al. ............... 382/240
6,825,838 B2 * 11/2004 Smith et al. ................... 345/419
6,939,138 B2 * 9/2005 Chosack et al. .............. 434/262
7,352,370 B2 * 4/2008 Wang et al. ................... 345/424
7,650,179 B2 * 1/2010 Redel et al. ................... 600/427
8,147,503 B2 * 4/2012 Zhao et al. .................... 606/130
8,162,835 B2 * 4/2012 Ichikawa et al. .............. 600/443
8,285,357 B2 * 10/2012 Gardner et al. ............... 600/407
2006/0069536 A1 3/2006 Butsev et al.
2007/0049817 A1 3/2007 Preiss et al.
2008/0227073 A1 * 9/2008 Bardsley et al. .............. 434/267
2009/0093702 A1 * 4/2009 Vollmer et al. ............... 600/407
2009/0162820 A1 * 6/2009 Tada et al. ..................... 434/272

FOREIGN PATENT DOCUMENTS

JP 2002-336247 A 11/2002

(Continued)

OTHER PUBLICATIONS

International Search Report and Written Opinion for PCT/GB2008/000636 mailed Sep. 12, 2008.

Ehricke, H.H., "SONOSim3D: A Multimedia System for Sonography Simulation and Education with an Extensible Case Database" Eur. J. of Ultrasound, vol. 7, No. 3, pp. (225-300) 1-9.

(Continued)

*Primary Examiner* — Katrina Fujita
(74) *Attorney, Agent, or Firm* — Knobbe, Martens, Olson & Bear, LLP

(57) ABSTRACT

There is disclosed a method of simulating the output of a medical imaging device, the medical imaging device being operable to image an anatomical structure, and the method including: accessing model data representing a model of the anatomical structure; accessing selection data representing a selected region of the anatomical structure to be imaged; and processing the selection data and the model data to generate output data representing a simulation of the output of the medical imaging device when imaging the selected region.

27 Claims, 18 Drawing Sheets

DISPLAY 1522
COMPUTER 1520
USER INPUT DEVICES 1524
1540
1542
1500
1550
1502
1544
1548
1546

(56) References Cited

FOREIGN PATENT DOCUMENTS

| | | | | |
|---|---|---|---|---|
| JP | 2003/178324 | | 6/2003 | |
| JP | 2003-310592 A1 | | 11/2003 | |
| JP | 2005/237825 | | 9/2005 | |
| JP | 2006-003856 A | | 1/2006 | |
| JP | 2007-148303 A | | 6/2007 | |
| WO | 2006/013813 A1 | | 2/2006 | |
| WO | 2006/036458 A1 | | 4/2006 | |
| WO | WO 2006/077338 | * | 7/2006 | ................ G06T 5/00 |
| WO | WO 2006/085564 | | 8/2006 | |
| WO | WO 2007/015365 | | 2/2007 | |
| WO | WO 2007/074668 | | 7/2007 | |
| WO | WO 2007/097247 | * | 8/2007 | ............... A61B 8/12 |

OTHER PUBLICATIONS

Maul, H. et al, "Ultrasound Simulators: experience with the SonoTrainer and comparative review of other training systems" Ultrasound Obstet Gynecol 2004, vol. 24, pp. 581-585, Published Aug. 4, 2004.

Tahmasebi, M. et al, "A Framework for the Design of a Novel Haptic-based Medical Diagnostic Simulator" Submitted to IEEE Transactions on Information Technology in Bio medicine Aug. 2006, http://research.cs.queensu.ca/~tahmaseb/Amir_website_files/TITB_2008_Amir_Tahmasebi.pdf.

Notice of Allowance dated May 14, 2014 of corresponding Japanese Patent Application No. 2010-548162 in 3 pages.

* cited by examiner

MEDICAL TRAINING METHOD AND APPARATUS

CROSS-REFERENCE TO RELATED APPLICATIONS

This application is the U.S. National Phase under 35 U.S.C. §371 of International Application No. PCT/GB2008/000636, filed Feb. 25, 2008, designating the United States and published in English on Jul. 23, 2009, as WO 2009/106784.

FIELD OF THE INVENTION

The present invention relates generally to facilitating medical training, but has further applications.

BACKGROUND OF THE INVENTION

Medical imaging devices provide an important diagnostic tool for many medical applications. One example of a medical imaging device is an ultrasound scanner. Ultrasound scans are carried out by transmitting high frequency ultrasonic sound into a human body and received and processing reflections of the transmitted sound in order to create an image of an organ or other structure in the body.

For diagnostic purposes, a medical professional performs an ultrasound scan using a hand-held probe (or more commonly referred to as a transducer) that is placed directly on and moved over the surface of the body. Essentially, the transducer transmits sound waves into the body and receives echoing waves that reflect from internal organs, fluids and tissues. The reflected waves are converted to corresponding electrical pulses that are transmitted to an electronic analyser, and displayed by a computer, which in turn creates a real-time image on a monitor.

Cardiac ultrasound, or echocardiogram, uses standard ultrasound technique to image two-dimensional slices of the heart. An echocardiogram allows a medical professional to analyse the heart beating and to visualise the structures of the heart in order to monitor the state of the heart and to diagnose cardiovascular diseases.

There are two main types of echocardiogram, namely, a transthoracic echocardiogram (TTE), and a transoesophageal echocardiogram (known as TEE or TOE).

TTE is a standard non-invasive procedure and is performed by placing the transducer on the chest wall, aiming an ultrasound beam through the chest and to the heart. Similarly, the transducer records the sound wave echoes as they reflect off internal structures of the patient's chest. In this procedure, the lungs and ribs may obscure the view, and a small amount of intravenous dye may be applied to improve the images.

Although TTE is considered a highly accurate procedure, the accuracy can be reduced because of obesity, chronic obstructive pulmonary disease, or chest-wall deformities. In these circumstances, TOE is recommended. In a TOE procedure, a flexible tube containing a transducer is guided down the patient's throat and into the lower part of the oesophagus. This procedure can allow a clearer two-dimensional echocardiogram of the heart.

As echocardiography becomes a widely used diagnostic tool, training and accreditation in echocardiography has also become vitally important. Training in echocardiography includes instruction in the basic aspects of ultrasound, performing echocardiographic examination to integrate understanding of three-dimensional cardiac anatomy, interpreting two-dimensional (2D) screen images and learning to build a mental model of the heart from multiple 2D images.

Thus, it is desirable to provide a realistic training device for training medical professionals in the use of echocardiography equipment and in the interpretation of resulting 2D ultrasound images.

A similar need can also arise in relation to other types of medical imaging device, such as magnetic resonance imaging (MRI) scanners, X-ray devices, and so on.

SUMMARY OF THE INVENTION

In consideration of the above issues, the present invention provides a method of (and corresponding apparatus for) simulating the output of a medical imaging device, by processing selection data and model data to generate output data representing a simulation of the output of the medical imaging device when imaging a selected region.

Further apparatuses and methods, including but not limited to a mannequin and a simulator probe, may also be provided. These further apparatuses and methods are not necessarily limited to the field of medical imaging devices.

BRIEF DESCRIPTION OF THE DRAWINGS

Embodiments of the present invention will now be described with reference to the accompanying drawings, in which.

GENERAL DESCRIPTION

Figure 1:
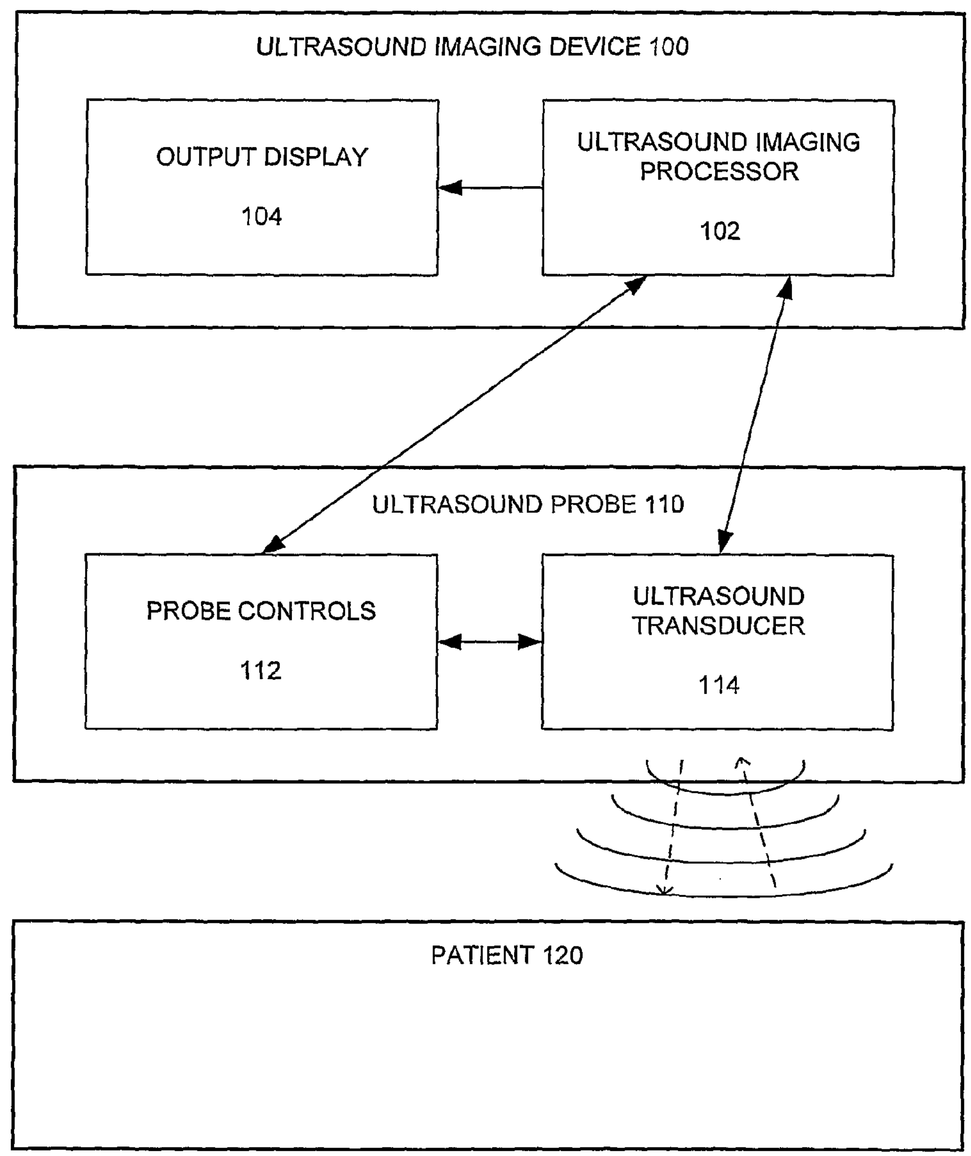
FIG. 1 is an illustration of the operation of a conventional ultrasound scanning device.

Before the embodiments shown in the attached figures are described in detail, a few general and non-limiting remarks will be made:

One embodiment provides a method of simulating the output of a medical imaging device, the medical imaging device being operable to image an anatomical structure, and the method comprising: accessing model data representing a model of the anatomical structure; accessing selection data representing a selected region of the anatomical structure to be imaged; and processing the selection data and the model data to generate output data representing a simulation of the output of the medical imaging device when imaging the selected region.

By accessing model data representing an anatomical structure in order to form output data representing a simulation of the output of a medical imaging device, a more versatile simulation can be provided. For example, a more accurate simulation can be provided if necessary by making appropriate refinements to the model.

The term "model" as used herein in relation to a structure preferably connotes a representation or description of the structure, and may in particular refer to a mathematical or geometric abstraction of component parts of the structure. Such a geometric abstraction may for example comprise a set of inter-linked polygons forming a complex surface or volume that approximates the surface or volume of the structure in question. The term "imaging" preferably connotes processing sensor inputs to form (ultimately) an image (or picture) that can be interpreted by a user (such as a medical professional, for example). A medical imaging device may relate to any device capable of performing an imaging function for use in therapeutic or surgical applications, for example, and may typically involve detecting electromagnetic, electrical, magnetic, sonic or other perturbations (which may be caused by the device) in order to determine the composition of a selected region (such as a surface or volume) of a patient's anatomy. The term "structure" may relate to a specific organ or body part, or may relate more generally to a non-specific region of anatomy enclosed within a given volume or area, for example. The selection data is discussed in more detail below, but may typically encode some form of user input, for example recording key presses on a keyboard or the selection of a point or region by a pointing device (such as a mouse) or other input device (in an embodiment where the method is carried out exclusively within a single computer apparatus, for example).

In one example described herein, the anatomical structure is the heart, and the medical imaging device is an ultrasound probe. In this example, the model data includes a 3-D definition of heart and associated sub-structures of the heart using polygonal modelling techniques. In this particular example, medical professionals can be provided with advanced medical training relating to the heart without having to rely on 'in vivo' techniques. Other examples of anatomical structure, medical imaging device and model data (amongst other things) are of course possible, and further examples are given below.

The step of processing the selection data and the model data may further comprise simulating image processing steps carried out by the medical imaging device. The process may include carrying out processing steps analogous to (or simulating) processes carried out by or in the simulated medical imaging device, such as image sharpening, overlaying simulated medical information, imaging cropping, gain and contrast adjustments, and so on. This can provide a more realistic simulation of the output of the medical imaging device, allowing a medical professional more directly to compare the simulated output and the real output.

The medical imaging device may include a sensor for sensing signals that have propagated through the patient, and wherein the step of processing the selection data and the model data further comprises simulating physical effects relating to the propagation of the signals. This can further improve the accuracy of the simulation overall. The simulation of the physical effects may comprise ray-tracing the signals (particularly if the signals are emitted from a known emitter, which may be the sensor or sensor probe itself, or a remote source as in the case of X-rays, for example), or taking into account physical phenomena relating to the propagation of certain types of signals, for example.

The step of processing the selection data and model data may further comprise rendering a portion of the model identified by the selection data in order to form an output image. The rendering can entail forming a 2-D or a 3-D representation of the selected region of the model, for example as an array of pixels or voxels (a conventional computer-readable 'image') or as a list of graphical operations (such as a 'vector graphics' image). The image may be displayable on a computer or other display using conventional display hardware, for example.

In more detail, the step of rendering a portion of the model includes the step of forming a cross-sectional image. Cross-sectional images are output by many medical imaging devices, because typically they are used to gain information about the interior structures of a patient. Medical training is required in particular to allow doctors to form a mental image of an anatomical structure based on a given cross-section or set of cross-sections of the structure.

The step of processing the selection data and the model data further comprises adding at least one visual artefact to said output image. In the case of ultrasound, for example, visual artefacts caused by a variety of mechanisms, such as the underlying physics of the energy-tissue interaction, or data acquisition error resulting from patient motion. Some more specific examples of physical effects and artefacts are given below.

For medical imaging devices that use a radial scanning principle, such as ultrasound transducers for example, it was observed that visual artefacts can occur in parallel with (or in some cases potentially transverse to) the signal propagation path. For these such devices, the step of generating said at least one artefact may further comprise: defining a polar coordinate space in relation to said output image, the polar coordinate space corresponding to a region swept by the radial scan; transforming said output image from the defined polar coordinate space into a planar coordinate space to form a planar-coordinate transformed image, the planar coordinate space having two orthogonal axes, one of said axes corresponding to the radial direction of the radial scan and the other of said axes corresponding to the sweep direction of the radial scan; processing at least one of individual rows and individual columns of said planar-coordinate transformed image in order to add visual artefacts to said planar-coordinate transformed image; and transforming said planar-coordinate transformed image back into the polar coordinate space.

By transforming the output image from a polar coordinate space into a planar coordinate space in order to add artefacts, and then transforming the image back into the polar coordinate space, the generation of artefacts can be carried out more efficiently, since in the planar-coordinate transformed image the individual signal paths have been separated into individual rows (or columns) of the image and can thus be processed independently of any other (depending on the scanning resolution, for example).

This feature is also provided in independent form. Accordingly, in another embodiment there is provided a method of generating an image to simulate the output of an imaging device, the imaging device being operable to carry out a radial scan, and the method comprising: receiving an image representing an approximation of the output of the imaging device; defining a polar coordinate space in relation to said image, the polar coordinate space corresponding to a region swept by the radial scan; transforming said image from the defined polar coordinate space into a planar coordinate space to form a planar-coordinate transformed image, the planar coordinate space having two orthogonal axes, one of said axes corresponding to the radial direction of the radial scan and the other of said axes corresponding to the sweep direction of the radial scan; generating at least one visual artefact and adding said at least one visual artefact to said output image, including the step of processing at least one of individual rows and individual columns of said planar-coordinate transformed image in order to add visual artefacts to said planar-coordinate transformed image; and transforming said planar-coordinate transformed image back into the polar coordinate space to form output image data.

The method may further comprise generating edge detection data, the edge detection data encoding information about edge transitions in the output image data. The edge detection data may for example include data encoding the position and/or qualities (such as the 'hardness') of the detected edges. The step of generating the edge detection data may comprise scanning the output image data to detect edges and recording characteristics about the detected edges in the edge detection data, or may for example comprise accessing the model data to determine a correspondence between edges represented by the model and the respective location in the output image data. It has been observed that many artefacts in the output of medical imaging devices relate to effects caused by edge transitions in the internal structures of a patient. The edge transitions may correspond to boundaries between different types of tissues, between solid structures and voids, between different structures, between the exterior and interior of the patient, and so on. By generating the edge detection data, a number of subsequent image processing steps can be simplified and/or made more efficient.

The step of generating said at least one visual artefact may include processing the edge detection data to add reverberation artefacts to the output image data, the reverberation artefacts representing ghost images caused from reflections of a probe signal at a number of the edge transitions. The processing may further include limiting the number of detected reflections to a finite number in order to reduce the total amount of processing, and also may include reduce the amplitude of the ghost images in dependence on the number of reflections that have occurred.

Additionally, or alternatively, the step of generating said at least one visual artefact may include processing the edge detection data to add shadow artefacts to the output image data, the shadow artefacts representing a masking of certain portions of the imaged region caused by the attenuation of a probe signal at a number of edge transitions.

Also, the step of generating said at least one visual artefact may include adding systematic artefacts to the planar-coordinate transformed image, the systematic artefacts having characteristics varying in dependence on one of the axes of the planar coordinate space. The systematic artefacts may be an image attenuation, for example, in which case the attenuation may have a strength characteristic that increases in amplitude with increasing distance along an axis corresponding to radial distance in the scan. This can cause the image to fade out in dependence on the distance from the simulated sensor, for example, which can help to simulate the effect of signal attenuation when the probe signals are emitted from a transceiver including the sensor (as is the case with ultrasound transducers, for example).

Other artefact types are of course possible, such as noise (guassian or otherwise), and other variations of characteristics are possible. For example, signal fading at the outer limits of the radial scan region can be implemented by attenuating the image in dependence on the transverse axis (that is, the axis corresponding to the radial scan angle), and in particular attenuating the image more at the extreme ends of that axis. In addition, scatter effects can be provided by inserting image noise (such as guassian noise) into the output image in dependence on the detected edge transitions.

In one embodiment, the output image data may include a plurality of columns of image elements; and the step of generating the edge detection data may comprise generating a sparse array of data representing the location of edge transitions, the sparse array having a plurality of columns, corresponding to respective columns of the output image data, and a plurality of rows, the value of each consecutive row of a particular column representing the location of each consecutive edge transition in the respective column of the output image data.

The output image data may be pre-processed using any of the polar to planar transformation methods as aforesaid, for example, in order to map each column of image elements to the signal path of one or more probe signals (as discussed above) in order to simplify the processing. It will be appreciated that the rows of the sparse array may be substituted for the columns of the sparse array and vice versa, if desired, and likewise for rows and columns of the output image data. The image elements may be pixels, for example, or rows or columns of voxels (three dimensional pixels) that may be further subdivided as appropriate. Each consecutive edge transition may advantageously be determined by scanning the relevant column of the output image data starting after the row corresponding to the last detected edge. The value of each entry in the sparse array may for example be a number encoding a row number in the output image data. The number may be encoded in any appropriate form, such as colour data (to allow processing of the sparse array by a graphics processing unit, GPU).

If the size of the output image data is m×n pixels, for example, the size of the sparse array may be m×s units (or indeed pixels), where s (the maximum number of rows required in the sparse array) is normally considerably smaller than n. Thus the edge detection information can be stored in a relatively small area of memory.

The step of generating a sparse array of data may comprise: creating a plurality of data vectors, each data vector corresponding to a row of the sparse array; processing each of the data vectors in sequence, the processing of each consecutive data vector accessing data in the respective preceding data vector; and combining the plurality of data vectors to form the sparse array of data.

The data vectors may advantageously be images having a size m×1 (where the overall size of the spare array is m×s, as discussed previously). This can allow each of the images to be processed by a graphics processing unit (GPU), reducing the load on a central processing unit (CPU). In addition, the highly parallel nature of GPUs can allow the values of each column in each image to be computed in parallel (this is possible in this case because the edges are detected within individual columns of the output image data, and thus the values for each column in the sparse array are entirely independent of the values in other columns). The values of different rows in a given column in the sparse array depend on other rows, and thus cannot be processed in parallel. By splitting the sparse array into a series of row 'slices', the parallel processing nature of the GPU can be harnessed to the maximum extent.

In another example, the step of generating said at least one visual artefact may include: accessing volumetric noise data representing the distribution of randomly-generated noise data values within a volume that encloses the anatomical structure; processing the volumetric noise data to map a number of the noise data values to elements of the output image data; and processing the output image data to superimpose the mapped noise data values onto the respective elements of the output image data.

This allows randomly-generated noise data values to be applied consistently and repeatably regardless of the selected region to be imaged (including the location and orientation). This can allow a realistic simulation of varying tissue densities and the like (which are similarly constant when viewed from different positions and orientations).

The volumetric noise data may comprise a plurality of voxels (an array or matrix of three-dimensional pixel values arranged along three orthogonal axes), for example, or may alternatively be generated algorithmically (more specifically, the seeds for a random number generator may be generated in dependence on an algorithm that includes the three ordinates identifying the point in the volume, for example).

It will be appreciated that the principles described above in relation to graphics processor units (GPUs) can be applied more generally to other aspects of the method. Accordingly, the step of processing the selection data and the model data further may comprise processing the selection data and the model data using a graphics processing unit, GPU.

In one embodiment, the method may further comprise accessing model parameter data defining at least one parameter of the model, and wherein the step of processing the selection data and the model data further comprises transforming the model using the model parameter data.

The model parameter data may include specifications or constraints relating to aspects of the model. For example the parameter(s) may specify scaling factors (such as length and width scaling factors, used in relation to defined orientations of the model) to be applied to specific portions of the model or to the model as a whole. The parameter(s) may also relate to timings, which may be absolute or relative to a point within a defined animation cycle. For example the model may deform repeatedly in accordance with a timing cycle, and the deformations may take place algorithmically in dependence on the parameter(s) or by using look-up tables or similar. The use of parameters can reduce the amount of memory storage required in order to display a number of related models.

The method may further comprise: receiving real medical imaging data relating to a real anatomical structure; and processing the real medical imaging data and the model data to generate the parameter data, by estimating parameters of the real anatomical structure. Here "real" is merely to contrast with "simulated". In other words, "real" medical imaging data is data output by a (non-simulated) medical imaging device, and the "real" anatomical structure is the anatomical structure imaged by the (non-simulated) medical imaging device. Bayesian or other statistical methods can be used to estimate the parameter data, for example. The parameters that can be estimated include parameters relating to dimensions, and parameters relating to timings, for example relating to relative timings within a cycle.

By combining the model of the anatomical structure with real medical imaging data information about the real anatomical structure can be presented in more abstract terms that may be more useful to a medical professional. For example, pathologies can be more usefully identified by comparing the parameterised model with a 'healthy' model. The parameter data may be stored or transmitted (see below), for example.

The step of generating the parameter data may further comprise: accessing imaging position data identifying the imaged region associated with the real medical imaging data; generating output image data for a region corresponding to the imaging position data; and determining the parameters by comparing the real imaging data and the output image data.

The imaging position data may be received from the medical imaging device directly or derived from information (such as text) overlaid on the real medical imaging data, for example, or may be estimated from the real medical imaging data with reference to the model data, for example.

The method may further comprise receiving the parameter data via a network. Alternatively, other appropriate input processes can be used (such as loading the parameter data from removable media attached to a host computer). This can allow specifically tailored versions of the model to be shared without requiring the transfer of the model (or sets of versions of the model) itself. This can facilitate the distribution of training and reference materials, for example, relating to certain pathologies of the relevant structure. It will be appreciated that the other items of data as aforesaid can also be shared by similar means. It will also be appreciated that the method may further comprise transmitting the parameter data via a network.

With regard to the timing parameters mentioned above, an alternative approach is possible: the method may further comprise accessing timing data, and the step of accessing the model data may further comprise selecting the model data from a plurality of sets of model data in dependence on the timing data. Thus, a plurality of versions of the model are stored and an appropriate version of the model is selected depending on the timing data, which may for example represent the current position in an animation cycle. It will be appreciated that other aspects can be controlled in a similar way. For example, an appropriate version of the volumetric noise data (as aforesaid) can also be selected depending on the timing data, with any necessary deformations made in order to correspond to the current version of the model.

If the timing data specifies a time period, the method may further comprise: selecting further model data from the plurality of sets of model data in dependence on the timing data, the first selected model data being associated with a time period prior to the specified time period and the further selected model data being associated with a time period subsequent to the specified time period; and interpolating the first selected model data and the further selected model data to generate interpolated model data. This can reduce the amount of storage required, by requiring fewer model data sets to be provided for a given total number of animation 'frames'. The time periods may be absolute timing values or time offsets within a defined animation cycle, for example.

In the embodiments relating to the anatomical structure, the model data may define a plurality of sub-structures of the anatomical structure, and the method may further comprise: receiving user selection data identifying a selected portion of the output image data; processing anatomical data, including anatomical information associated with each of the sub-structures, to select anatomical data associated with the selected portion of the output image data; and outputting the selected anatomical data.

This can improve the usefulness of the method for training medical professionals, by allowing relevant anatomical data to be outputted (and displayed, in the vicinity of the output image, for example) when a user selection is made of a particular portion of the output image. The anatomical data may include the name and/or description of a selected sub-structure, and may also include hierarchical information, for example, showing the relative arrangement of the selected sub-structure within a hierarchy of sub-structures. The user selection data may include a pixel (or voxel) coordinate within the output image data (such as an x and y position, or the like), or may include an identification of a selected region covering a number of pixels or voxels, or the like. The user selection data may be generated in dependence on one or mouse clicks by the user, or the equivalent for other types of input device.

The method may further comprise: accessing volumetric selection data representing the identity of relevant sub-structures at a plurality of points within a volume that encloses the anatomical structure; processing the volumetric selection data to determine a point in the volumetric selection data corresponding to the user selection data, and to determine a relevant sub-structure associated with that point, the anatomical data is selected in accordance with the relevant sub-structure. This can provide a computationally more efficient way to identify selected sub-structures. The volumetric selection data may advantageously be stored in a volumetric 'texture' that is suitable for processing by a graphics processing unit (GPU).

In one embodiment the volumetric selection data is capable of associating a plurality of sub-structures with each point in the volume, and the step of processing the volumetric selection data further comprises: determining if a previously selected sub-structure is associated with the point in the volumetric selection data corresponding to the user selection data and, if so, selecting the next sub-structure associated with the point in the volumetric selection data, such that repeated user selections corresponding to the same point in the volumetric selection data will cycle through all associated sub-structures.

This can provide a simple user interface to allow the convenient selection of a potentially very large number of sub-structures. The sub-structures for each point may advantageously be arranged in ascending or descending order in the hierarchy, so that repeated clicks on the same portion of the image cause the selection of an increasingly large (or small) sub-structure. For example, a particular point in volumetric selection data for a heart (say) may contain the identify of sub-structures relating to the surface of a ventricle, the ventricle itself, a particular side of the heart, and the heart itself (in increasing order in the hierarchy of features).

The volumetric selection data may be accessed in dependence on a timing parameter specifying a time period, in which case the method may comprise deforming the volumetric selection data in dependence on the time period, or alternatively the method may further comprise: selecting further volumetric selection data in dependence on the timing parameter, the first selected volumetric selection data being associated with a time period prior to the specified time period and the further selected volumetric selection data being associated with a time period subsequent to the specified time period; and interpolating the first selected volumetric selection data and the further selected volumetric selection data to generate interpolated volumetric selection data.

This can allow accurate selections to be made during the course of an animation cycle, for example, when parts of the model associated with particular sub-structures may deform significantly. The time period may be the time period as aforesaid. The step of interpolating the volumetric selection data may advantageously include the step of processing volumetric vector data, the volumetric vector data indicating for each point in the volumetric selection data where the point has moved from (or to) relative to the previous (or subsequent) volumetric vector data set in an animation cycle. This can provide improved results compared to 'fade through' techniques.

The method may further comprise outputting a plurality of output images, the plurality of output images forming an animation sequence. The output images can be output in a continuous and real-time fashion, for example, to provide a 'live' simulation.

The method may further comprise: receiving positional data representing the position of a simulated sensor of the simulated medical imaging device; processing the positional data to identify the relative position of the simulated sensor with respect to the simulated anatomical structure; and generating the selection data in dependence on the relative position of the simulated sensor. This can improve the accuracy of the simulation by allowing the selection of regions to be made using tools more closely approximating the real controls of the medical imaging device.

The term "position" may include a location (for example in 3D, as might be specified by x, y and z coordinates in a cartesian coordinate system) and/or an orientation (for example which might be specified by a 2D or 3D vector, or one of more of azimuth, orientation and elevation angles defined with reference to an appropriate datum), for example.

The positional data may include a representation of the position of the simulated sensor, and the positional data may include a representation of the position of a reference point on a simulated probe, the simulated sensor being provided on the simulated probe at a position remote from the reference point. With a knowledge of the dimensions of the simulated probe, the simulated sensor position can be inferred by an appropriate vector (or other) calculation based on the position of the reference point.

If the simulated probe includes at least one degree of freedom, the positional data may include state information regarding said at least one degree of freedom. The degree(s) of freedom may include the ability to cause the probe to flex at the tip in one or more directions, for example. More complicated probes are also possible, with a controllable flexing along their length. The state information depends on the nature of the degree of freedom. It may relate to an angular deformation, for example. In the above example with the flexing probe tips, the state information may for example include the current position of a dial that is operative to control the flexing (and from this the angular deformation can be inferred). In another example, the degree of freedom may be a distance traveled by the probe through a channel (such as the oesophagus, for example), and the state information may include the length traveled through the channel (or a measurement from which this length can be determined). Such a channel may be contorted into a complicated path, in which case there clearly may not be a straightforward correlation between the length traveled by the probe and the location and orientation of the probe sensor. Intrinsic coordinate functions can be used in this instance, for example, to obtain the location and orientation of the probe tip.

The method may be used with a mannequin to simulate the patient. In this case, the step of processing the positional data may further comprise accessing mannequin model data representing a model of the mannequin. The mannequin model data may be sufficient merely to allow a computation of the position of the simulated sensor, as aforesaid. For example, the mannequin model data can be a formula defining the shape of the channel down which the simulated probe passes. Alternatively, a more detailed model can be provided, for example including a three-dimensional representation of the interior and/or exterior surfaces of the mannequin. In this case, partially incomplete positional data can be resolved into a complete position using the mannequin model data (by applying the appropriate constraints and/or parameters to the model).

The method may further comprise receiving calibration positional data, and the step of processing the positional data may further comprise adjusting the received positional data using the calibration positional data. This can allow the location of a real probe (and hence the position of the simulated sensor) to be determined in relation to the mannequin despite the positional data not defining a position relative to the mannequin (for example, because the positional data is not defined using intrinsic or relative coordinates). The calibration positional data can be provided during a calibration phase, for example by placing the probe in a known or predefined location relative to the mannequin.

The anatomical structure may be an organ of the human or animal body, and may in particular be any one or more of the heart, lung, lungs, stomach, liver, kidney, and kidneys. By taking into account the various methods discussed earlier, it will be appreciated that the method may be applicable in particular to organs having complicated structures and/or 'dynamics' (like the heart).

The medical imaging device may be any one of an ultrasound transducer, an x-ray apparatus, a magnetic resonance imaging apparatus, and a positron-emission tomography device, for example, but is not limited to this selection. Clearly other medical imaging devices can be simulated where appropriate.

In another embodiment, the method further comprises: accessing medical device positional data representing the position of a medical device for insertion into the patient; and adding image data relating to the medical device to the output image data. This can allow the visualisation of an operation in which a medical device (such as a stent or other implant) is inserted into a patient and monitored via an appropriate imaging device. This method may further comprise: accessing medical device model data representing a model of a medical device for insertion into the patient; and generating the image data using the medical device model data. This can allow an accurate representation of the medical device to be overlaid on the simulated image. The image processing steps as aforesaid can be applied also to the representation of the medical device. In addition, medical device positioning data may be generated in dependence on user input. The positioning data can be updated, for example, in response to user input via conventional computer input methods (keyboard and pointing device, for example), or in response to a simulated medical device insertion procedure, which can be implemented in similar ways to the implementation of the simulated probe as aforesaid.

In another embodiment there is provided an apparatus for simulating the output of a medical imaging device, the medical imaging device being operable to image an anatomical structure, and the apparatus comprising: model data access means for accessing model data representing a model of the anatomical structure; selection data access means for accessing selection data representing a selected region of the anatomical structure to be imaged; and selection data and model data processing means for processing the selection data and the model data to generate output data representing a simulation of the output of the medical imaging device when imaging the selected region.

In a further embodiment there is provided an apparatus for facilitating training in relation to a medical imaging device for imaging a patient, comprising: a mannequin simulating the patient; a simulator probe for simulating a probe of the medical imaging device; and an imaging apparatus as aforesaid. The mannequin may include a channel for receiving the simulator probe (such as an approximation of the oesophagus, for example, or any other body cavities).

The apparatus may further comprise positioning means for determining the position of the simulator probe, the positioning means being operable to transmit positional data to the imaging apparatus. The positioning means may transmit the positional data using any convenient method, such as a USB connection, wireless transceiver, and the like. The positioning means may include a length measurement device for determining the length traveled by the probe within the channel. The length measurement device may for example be a sprung reel attached to the end of the probe, for example, operable to determine the number of rotations of the reel and hence the length of extension. Other techniques can be used for determining the position of the probe and/or simulated sensor, including triangulation techniques using magnetic sensors and/or radio frequency transmitters and receivers, for example.

The positioning means may include an accelerometer (or similar device, such as a gyroscope) mounted in the probe, for tracking at least one of the location and orientation of the probe. This can allow the probe to be moved freely around and inside the mannequin, for example.

The positioning means may include at least one user-controllable input device for configuring an aspect of the probe. The aspect may be the deformation of the tip or other portion of the probe, for example, and may be a rotating dial, button, or other control device. Advantageously, the user-controllable input device may mirror the provision of similar devices on the real probe.

The apparatus may further comprise a calibration reference location, and the positioning means may accordingly be configured to transmit calibration positional data when the probe is located in the calibration reference location. The calibration reference location can be a defined position such as the probe being fully inserted into the channel, or being placed on a specially marked position on the mannequin, for example.

The mannequin may further comprises an internal structure simulating the rib cage of the patient. The can give the necessary resilience and firmness, as well as external surface definition, to more accurately simulate the patient.

The mannequin may further comprise a deformable outer membrane to simulate the skin layer of a patient. Since some imaging techniques, such as ultrasound, are transcutaneous (carried out through the skin), a more accurate rendition of the skin layer can enhance the accuracy of the simulation. The deformable outer membrane may include silicone, rubber or other suitable deformable material.

In a related embodiment there is provided a mannequin for facilitating training in relation to imaging a patient with an ultrasound transducer, the mannequin comprising: an internal structure simulating the rib cage of the patient; a deformable outer membrane to simulate the skin layer of a patient; and means (such as a sensor) for determining the location and orientation of a simulated ultrasound probe applied to the mannequin, to allow the simulation of an ultrasound inspection of the patient. The mannequin may further comprise a channel for receiving the simulated ultrasound probe, to allow the simulation of an invasive ultrasound inspection of the patient.

Another embodiment provides a method of facilitating training in relation to a medical imaging device for imaging a patient, comprising: providing a mannequin simulating the patient; providing a simulator probe for simulating a probe of the medical imaging device; and carrying out a method as aforesaid.

In a further embodiment there is provided a computer comprising: an instruction memory storing processor implementable instructions; and a processor operable to process data in accordance with instructions stored in the instruction memory; wherein the instructions stored in the instruction memory comprise instructions for controlling the processor to perform a method as aforesaid.

The computer may further comprising a graphics processor unit, GPU, operable to carry out a portion of the step of processing the selection data and the model data.

The embodiments described herein can be implemented in any convenient form, for example using dedicated hardware, or a mixture of dedicated hardware and software. The present invention is particularly suited to implementation (in part) as computer software implemented by a workstation or laptop computer (in the case of the method and apparatus for outputting a simulated image) or server system (in the case of transmitting and receiving parameter data, for example parameter data encoding pathologies of particular anatomical structures). The invention may further comprise a network, which can include any local area network or even wide area, conventional terrestrial or wireless communications network. The systems may comprise any suitably programmable apparatus such as a general-purpose computer, personal digital assistant, mobile telephone (such as a WAP or 3G-compliant phone) and so on. Aspects of the present invention encompass computer software implementable on a programmable device. The computer software can be provided to the programmable device using any conventional carrier medium. The carrier medium can comprise a transient carrier medium such as an electrical, optical, microwave, acoustic or radio frequency signal carrying the computer code. An example of such a transient medium is a TCP/IP signal carrying computer code over an IP network, such as the Internet. The carrier medium can also comprise a storage medium for storing processor readable code such as a floppy disk, hard disk, CD ROM, magnetic tape device or solid-state memory device.

Although each aspect and various features of the present invention have been defined hereinabove independently, it will be appreciated that, where appropriate, each aspect can be used in any combination with any other aspect(s) or features of the invention.

DETAILED DESCRIPTION

The various embodiments mentioned above will be described in further detail with reference to the attached figures.

First, conventional medical imaging devices will briefly be described with reference to FIGS. 1 to 3.

FIG. 1 is an illustration of the operation of a conventional ultrasound scanning device.

An ultrasound imaging device 100 and an ultrasound probe 110 are used to image anatomical structures within the patient 120. The imaging device 100 includes an ultrasound imaging processor 102 for controlling the generation of appropriate ultrasound signals and for interpreting the received ultrasound reflections, and an output display 104 for outputting the result of the processing by the processor 102. The probe 110 may include probe controls 112 (as is discussed in more detail below), and an ultrasound transducer 114 for generating and receiving the ultrasound waves.

In use, input devices (not shown) can allow various properties of the ultrasound scan to be controlled, in dependence on the type of structure being imaged, for example. The ultrasound transducer picks up reflections from boundaries between volumes of differing densities. From this information, the ultrasound imaging processor 102 builds up an image of the internal structures of the patient.

Ultrasound imaging can be carried out externally, by applying the transducer 114 on the skin. However, some structures in the body (such as ribs and other bones) can block ultrasound waves, making it difficult to image certain parts of the body such as the heart and lungs. Consequently, ultrasound is also used internally, as will now be described with reference to FIG. 2.

Figure 2:
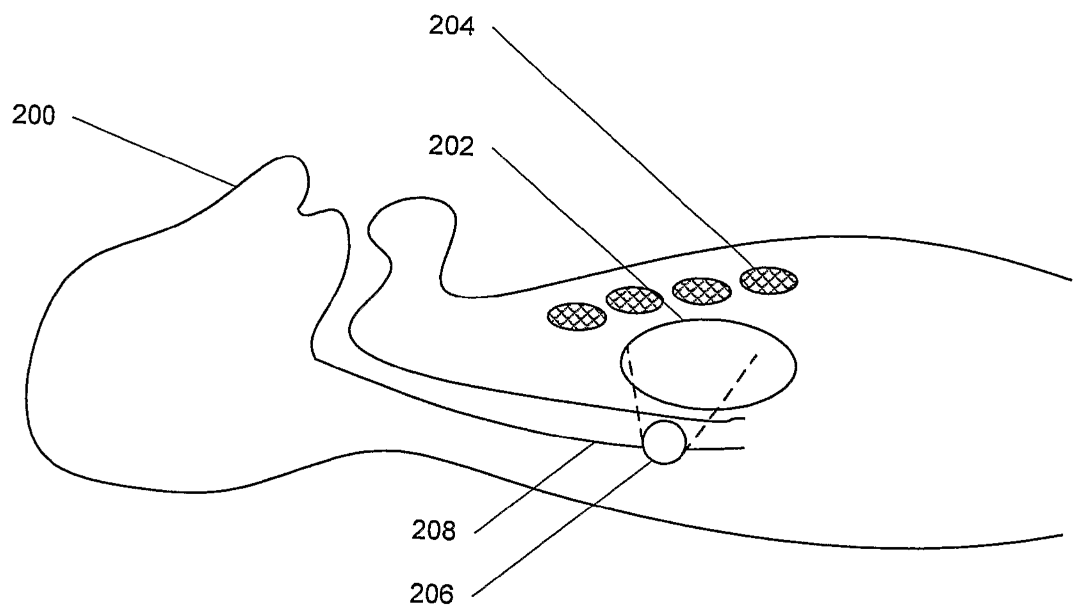
FIG. 2 is a schematic cross-section of a patient, illustrating a transoesophageal echocardiogram (ultrasound inspection) procedure.

FIG. 2 is a schematic cross-section of a patient, illustrating a transoesophageal echocardiogram (ultrasound inspection) procedure.

In FIG. 2, the patient 200 is shown schematically. A major internal organ 202, such as the heart, is shown. The ribs 204 are also shown, and it can be appreciated that these block a line of sight (LOS) between the exterior of the chest (the top of the figure) and the organ 202. Consequently, an ultrasound inspection can be carried out by positioning an ultrasound transducer in the position marked 206 (or similar). This can be done by feeding the transducer down the oesophagus 208 (under general anaesthetic, for example). The dashed lines emanating from the position 206 indicate a typical field of view of the sensor.

Figure 3:
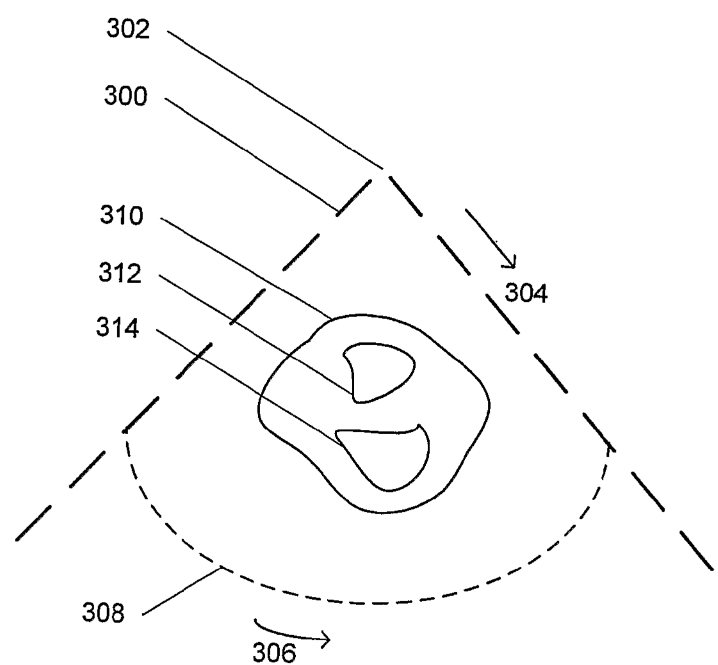
FIG. 3 is an illustration of a typical output from an ultrasound imaging device.

FIG. 3 is an illustration of a typical output (in schematic form) from an ultrasound imaging device such as the device 100 described above.

The output image is cropped into an approximate cone shape 300, representing the extent of the ultrasound scan. The scan can be mapped into polar coordinate space, with the apex 302 representing the origin of the coordinate space, the radial direction indicated schematically with arrow 304, and the angular direction indicated schematically by arrow 306. The dotted line 308 schematically indicates a line of constant radius relative to the origin. The radial direction in this coordinate scheme corresponds to increasing distance away from the ultrasound transducer. The scan essentially illustrates a two-dimensional cross-section through an anatomical structure, limited by the angular extent of coverage and the maximum radius. In this example, corresponding to the arrangement of FIG. 2 where the organ 202 is the heart, for example, FIG. 3 shows a cross-section through the heart 310, showing the sub-features of a first chamber 312 and a second chamber 314.

In practice, an ultrasound image contains many visual artefacts, arising from physical effects such as reverberation, shadowing, scattering and differing tissue densities, for example.

Because ultrasound (and other similar imaging techniques) display only a two-dimensional cross-section of an anatomical structure, it can be difficult for a medical professional to visualise the underlying three-dimensional structure. In addition, structures such as the heart are constantly changing in accordance with a defined cycle of muscle movements. This can increase the complexity of the visualisation process.

A first embodiment will now be described with reference to FIGS. 4 to 14. This embodiment concerns a system for simulating the output of an ultrasound scanning device, for example to allow medical professionals to be trained to recognise and to visualise underlying anatomical structures based on simulated ultrasound images.

Figure 4:
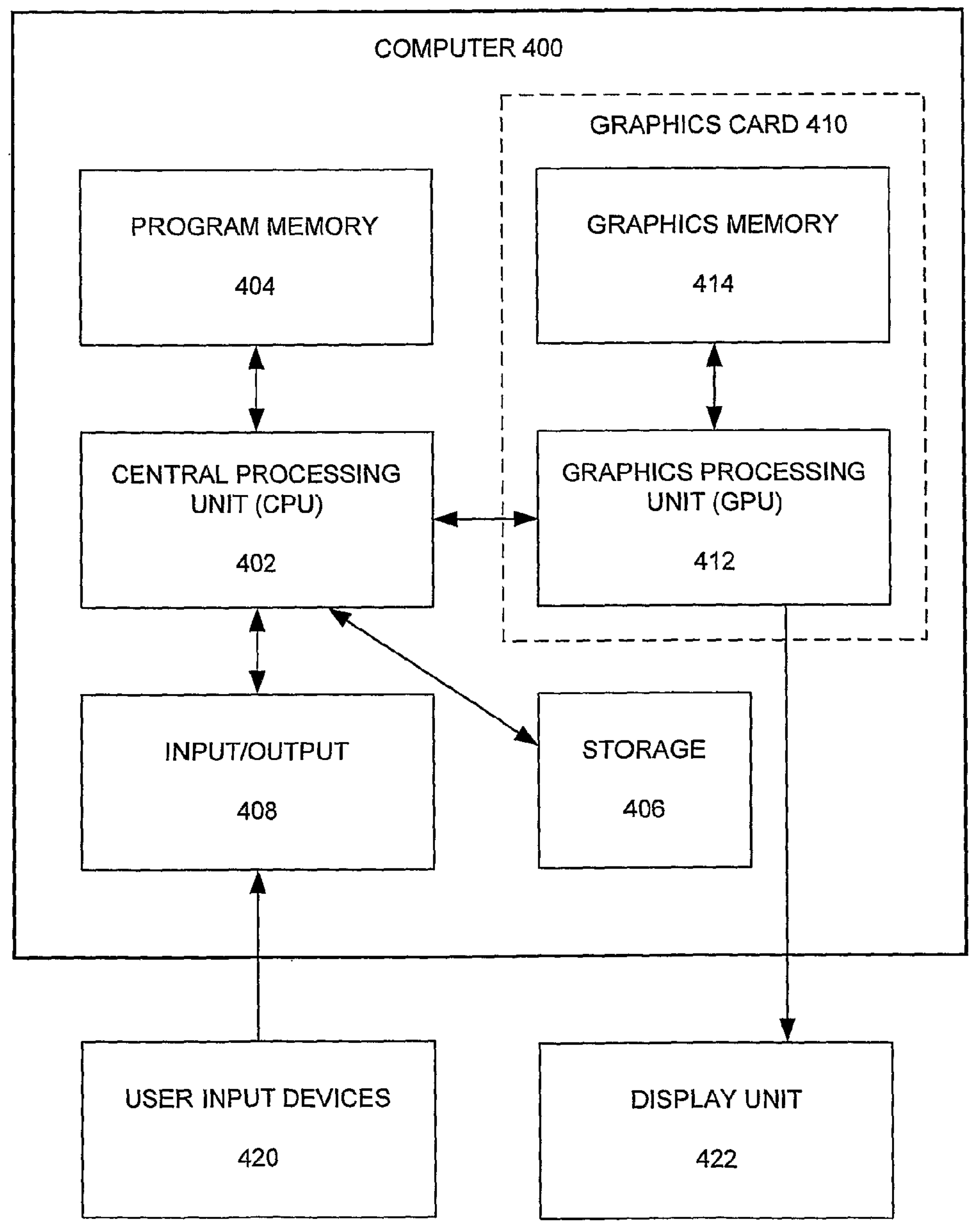
FIG. 4 is a schematic illustrating the components of a typical computer system suitable for use with a first embodiment.

FIG. 4 is a schematic illustrating the components of a typical computer system suitable for use with the present embodiment.

The computer 400 includes a central processing unit (CPU) 402, program (and program data) memory 404, storage 406 (such as a hard disk or similar), an input/output module 408, and a graphics card 410, including a graphics processing unit (GPU) 412 and dedicated graphics memory 414. User input devices 420 and a display unit 422 may be attached to the computer 400.

The CPU 402 controls and coordinates the overall execution of programs within the computer 400, in dependence on the user input that is provided via the input/output module 408. Some tasks, especially those related to the generation of graphical outputs, are delegated to the GPU 412 by the CPU 402. The GPU 412 undertakes its delegated tasks using its dedicated memory 414 to increase its efficiency (for example to store commonly used graphics ‘textures’). Program code may be transferred to the memory 404 from the storage device 406 under the control of the CPU 402.

Figure 5:
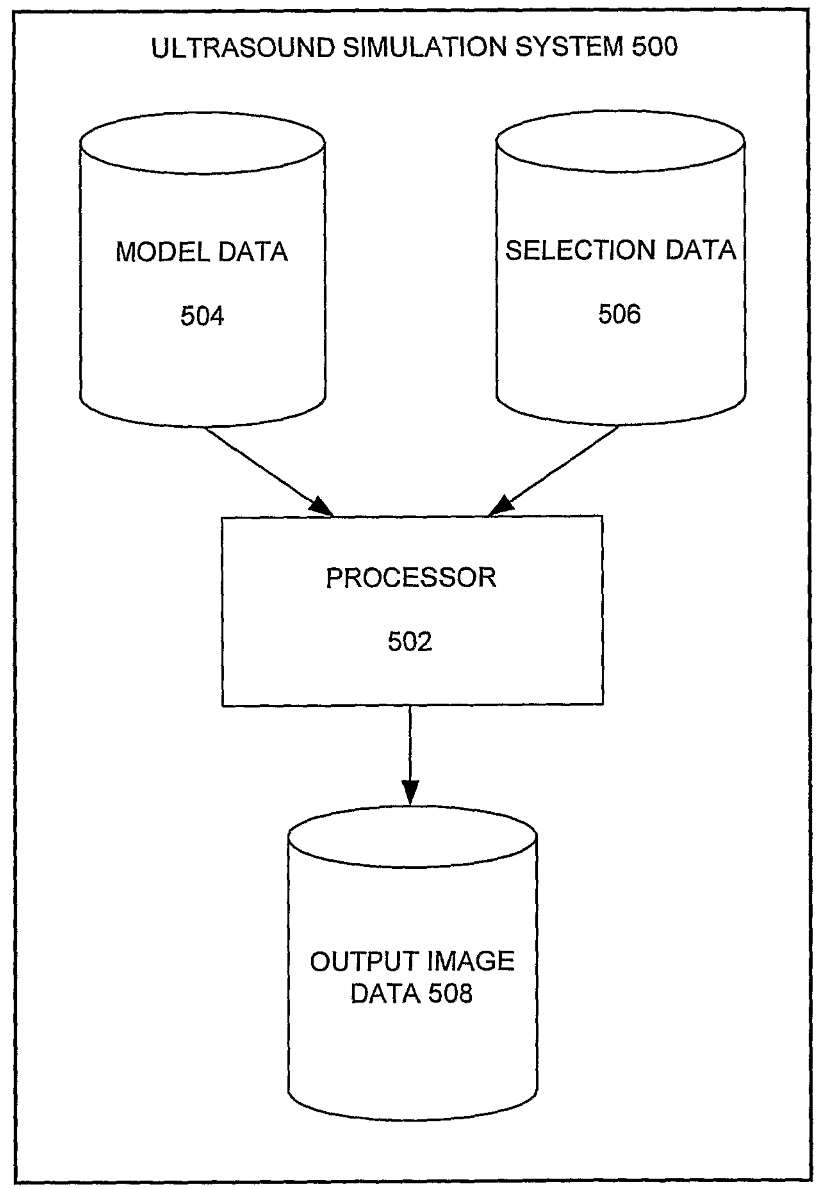
FIG. 5 is a schematic illustrating the components of an ultrasound simulation system in accordance with the first embodiment.

FIG. 5 is a schematic illustrating the components of an ultrasound simulation system in accordance with the first embodiment. The system is designed to simulate a transoesophageal echocardiogram (ultrasound inspection) of the heart. The heart is a particular subject of ultrasound training because it has very complex internal structures and is continuously moving, increasing the difficulty of visualisation from a two-dimensional ultrasound image.

In FIG. 5 the ultrasound simulation system 500 includes a processor 502 (such as the CPU and/or GPU of FIG. 4), a model data store 504 for storing a model of the heart, selection data 506 representing a selected region of the heart to be imaged, and an output image data store 508 for storing the output simulation images.

In use, the processor 502 processes the model data 504 and the selection data 506 to generate the simulated image 508. In forming the image 508, the processor (which may be the CPU and/or GPU) executes a number of process steps to simulate the processing carried out by the ultrasound imager that is being simulated, as well as a number of process steps to simulate physical effects relating to the propagation of the ultrasound signals.

The model data 504 will now be described in more detail with reference to FIG. 6.

Figure 6:
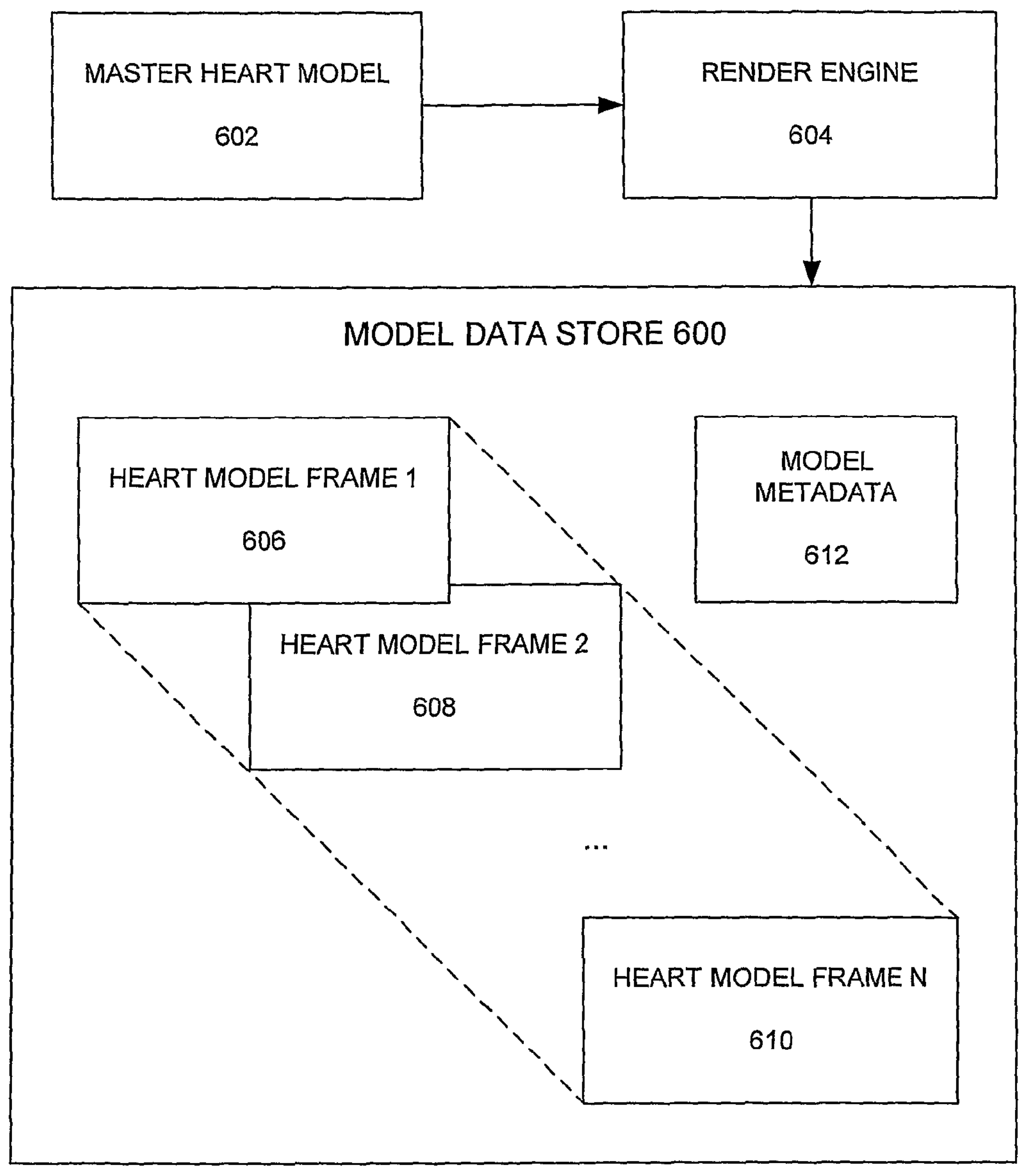
FIG. 6 is an illustration of the data structure within the model data store of FIG. 5.

FIG. 6 is an illustration of the data structure within the model data store 504 of FIG. 5.

The model data store 600 is shown, as is a master heart model 602. The master heart model 602 is a three-dimensional model of the heart, created using conventional three-dimensional modelling techniques. In the present embodiment, for example, the master heart model comprises a plurality of surfaces formed from polygonal primitives (basic building blocks) and including surface texture information (to control the appearance of the model). In addition, time-dependent deformations are applied to the master heart model 602 in order to simulate the movement of the heart throughout the cardiac cycle, again using conventional three-dimensional modelling techniques. A render engine 604 is also provided to convert the master heart model into the models in the model data store 600 (see below).

The model data store 600 includes a plurality of models, each model corresponding to a frame of animation of the heart cycle. Accordingly, a first heart model frame 606, a second heart model frame 608, and so on are provided, up to the heart model frame 610 for the nth frame of animation (for a total of n frames). The render engine 604 essentially takes a snapshot of the master heart model at the relevant time offset and stores the resulting deformed version of the model in the heart data store 600.

As a result of the rendering operation, the animation of the heart is simplified, because instead of deforming the model (which may be computationally-intensive) the processor simply has to select the appropriate model version.

By interpolating between stored models 606, 608, 610, the ultrasound simulator is able to generate model data representing time periods that fall between the defined animation frame time periods. Conventional interpolation methods are used. For example, a weighted average can be taken of the x, y and z coordinates of each of the polygon vertices in two adjacent models.

In addition, the model data store 600 includes model metadata 612 that contains information about the model. The metadata 612 includes additional information about the model, such as grouping information that identifies different parts of the model.

In use, the selected or interpolated heart model is rendered to display a three-dimensional representation of the heart at the particular point in the cardiac cycle. In addition, a further rendering is carried out to form the simulated ultrasound image.

The processing of the model data will now be described in more detail with reference to FIGS. 7 and 8.

Figure 7:
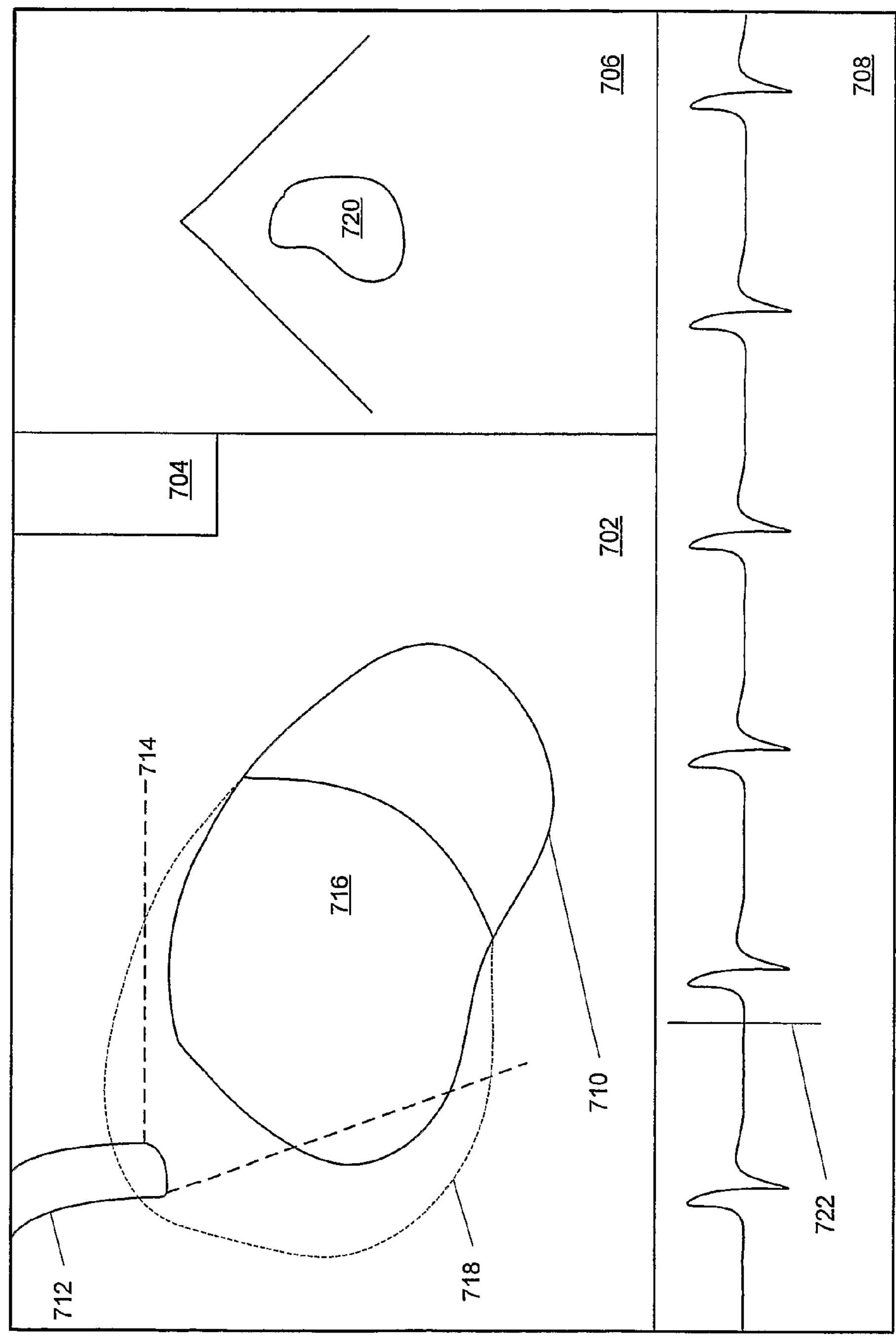
FIG. 7 is a schematic illustrating the screen display of the ultrasound simulator system.

FIG. 7 is a schematic illustrating the screen display of the ultrasound simulator system.

The screen display 700 includes a three-dimensional view 702 of the heart and imaging probe, a summary 704 of the controls and configuration of the simulated ultrasound probe, a simulated ultrasound imager output 706, and a timeline 708 with the cardiac cycle imposed on it.

In the three-dimensional view 702, the heart 710 and the transoesophageal probe 712 is shown. The field of view 714 of the probe is shown. Where the field of view 714 intersects with the heart 710, a cross-section 716 through the heart is shown, and the remainder 718 of the heart is shown in wireframe/semi-transparent view (to allow the cross-section 716 to be shown).

In the imager output window 706 a simulated ultrasound image is shown. The cross-sectional image 720 corresponds to the cross-section 716 shown in the three-dimensional view 702, but also includes artefacts and additional image processing to better simulate the ultrasound output.

In the timeline 708, the current time 722 is shown.

In use, the user can control the position and orientation of the probe using a variety of keyboard inputs and by clicking and dragging with the mouse. The field of view 714 changes correspondingly, and in turn so do the cross-sections 716, 720. The field of view 714 represents a selection of a region in the heart to be imaged. This selection corresponds to the selection data 508 of FIG. 5.

Figure 8:
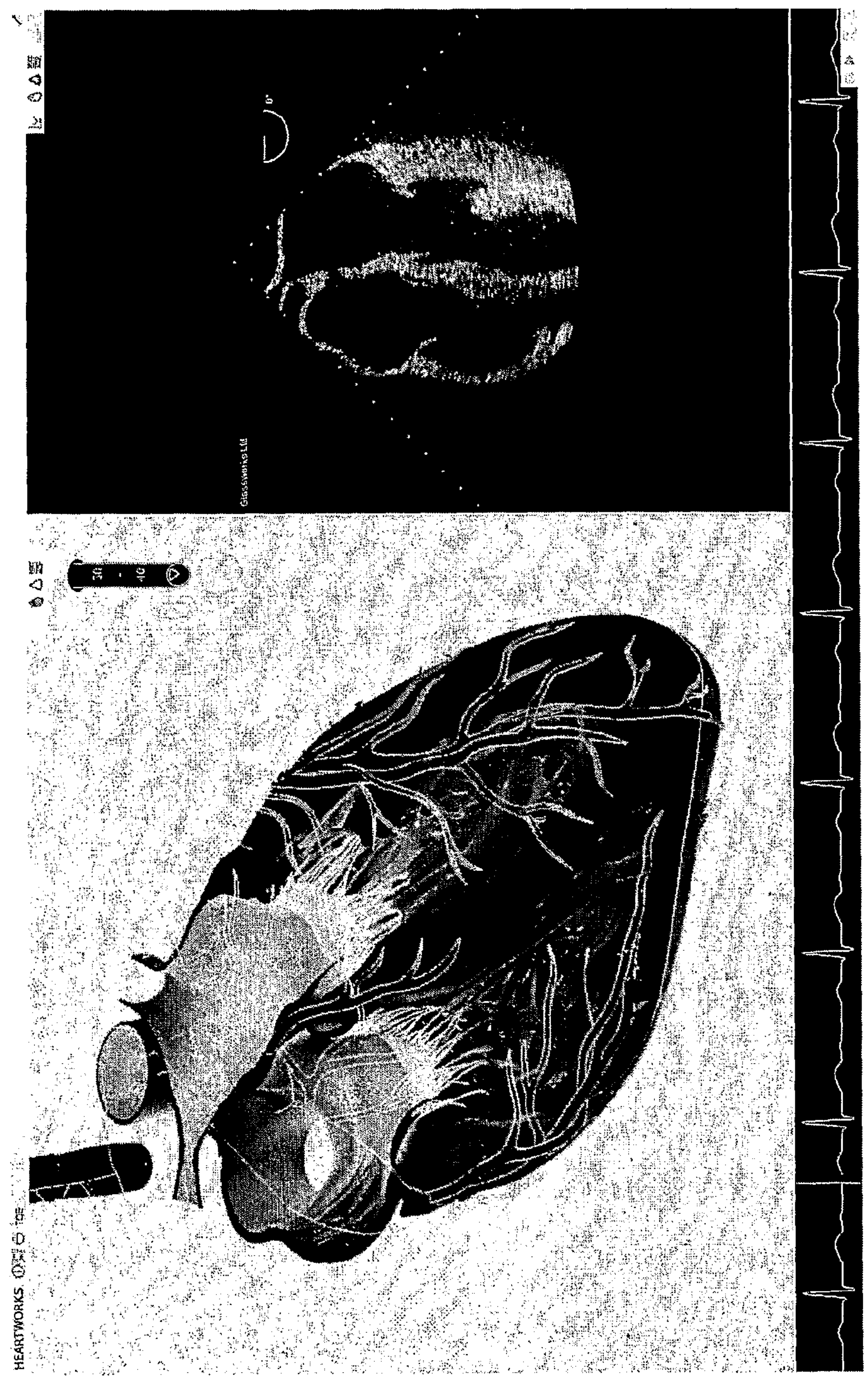
FIG. 8 is a screenshot of the screen display of the ultrasound simulator system.

FIG. 8 is a screenshot of the screen display of the ultrasound simulator system.

This screenshot is corresponds to the schematic of FIG. 7.

It will be appreciated that different views of the model and/or simulation window are possible. For example, in one mode, the heart is rendered in entirely solid form. In other modes, different parts of the model can be selected and the display of each part can be turned on or off independently. In addition, sections of the model can be selected by clicking in the relevant part of the three-dimensional view 502 or the simulator output window 504. Some of these features will be described in more detail below.

The user may also rotate the 'virtual' heart to examine the exterior of the virtual heart at different angles, and the user can also 'zoom into' the heart to obtain a close-up view.

In the present embodiment the OpenGL Application Programming Interface (API) is used to render the various views of the modelled heart. Other interfaces may be possible, although some of the processes use functions from the Extended OpenGL API (for reasons of computational efficiency), and these may not necessarily be supported elsewhere.

Figure 9:
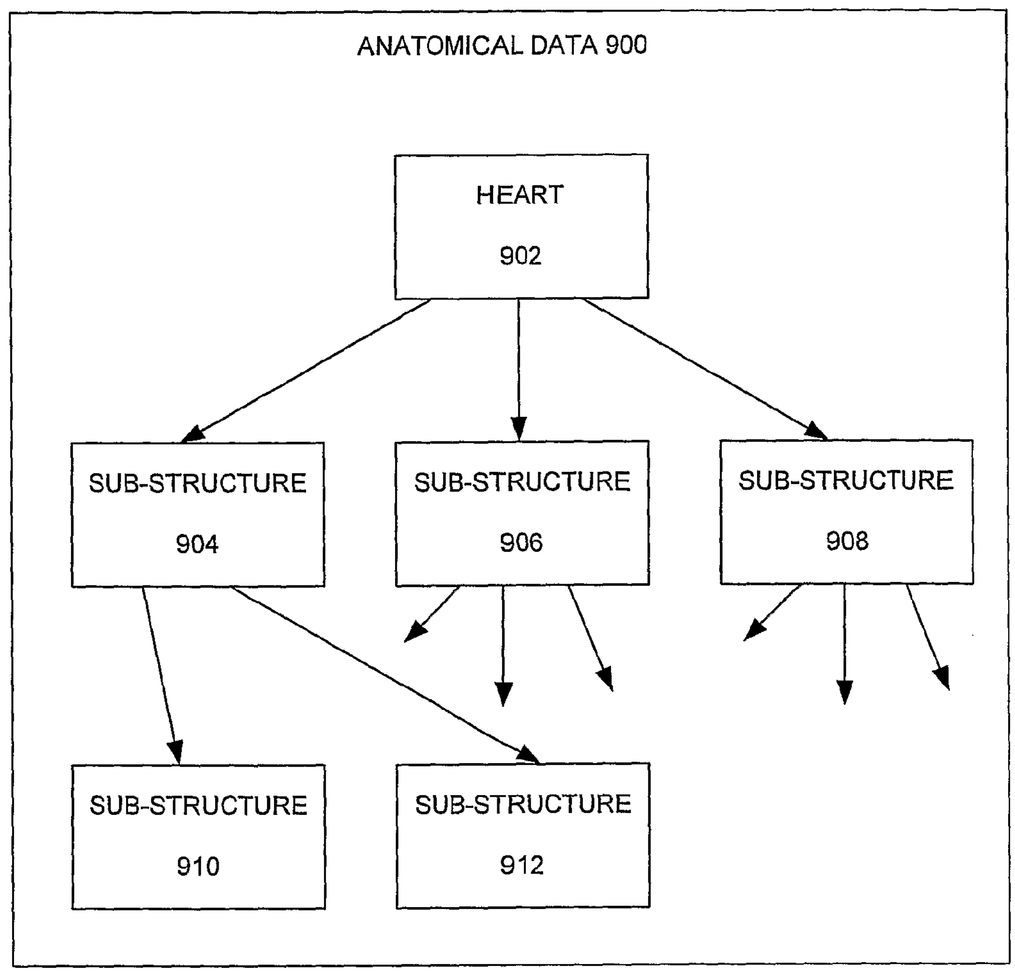
FIG. 9 is an illustration of anatomical data used in the present embodiment.

FIG. 9 is an illustration of anatomical data used in the present embodiment.

The anatomical data 900 includes hierarchical data defining the internal structure of the heart model. The heart anatomical data 902 has sub-elements 904, 906, 908. In turn, the sub-elements 904, 906, 908 may have further sub-elements 910, 912. Thus a hierarchy is defined.

The anatomical data 900 includes information about each of the structures of the heart (such as the ventricles, veins, and so on), and can be displayed in the main screen display of FIGS. 7 and 8, for example. The anatomical data also defines the parts of the model (in the present embodiment, a set of polygons) that correspond to the relevant anatomical structures. This allows the functionality described above of allowing certain parts of the model to be turned on and off, for example.

Further data is provided to allow the selection of each of the sub-elements of the heart. In particular, a volumetric 'selection texture' is provided (not shown). The texture has a plurality of voxels (volumetric pixels) arranged in a three-dimensional array. Each voxel has data associated with it that encodes the identity of any sub-elements associated with the given point. Thus, when the user clicks on a particular point on the three-dimensional model or on the two-dimensional simulated image, the system calculates the three-dimensional location of the click (using conventional algorithms), and then 'looks up' the nearest voxel in the selection texture.

Because each voxel may correspond to a plurality of substructures (because of the hierarchy of features), the system uses a further algorithm to determine which sub-structures should be selected. When a new selection is made, the system determines whether or not the previously selected sub-structure is associated with the selected voxel. If it is, then the next sub-structure in the list is selected. Otherwise the first substructure is selected. This algorithm ensures that all substructures associated with a particular point can be selected, and runs through the sub-structures in an orderly fashion (the sub-structures are ordered for each voxel in terms of hierarchy).

In the present embodiment, a single selection texture is generated, and deformed in dependence on the timing value. To do this, a technique is used which is similar to that described in "Harmonic Coordinates for Character Articulation" (Joshi et Al, ACM Transations on Graphics (TOG), July 2007, Vol. 26, issue 3).

Broadly speaking, this paper describes a technique for parametrising the interior volume of a mesh in terms of its vertices, such that the effect of deforming of the mesh can be determined at any point within its interior volume. The paper describes this technique specifically as a mechanism for deforming a mesh using an arbitrary lattice.

In the present embodiment the same approach is taken to parametrise the interior volume of the heart model to achieve deformation of 3D textures (in real-time). The present embodiment utilises a reverse spatial-mapping, whereas the Pixar paper essentially describes a forward spatial-mapping. To achieve this mapping a technique is used to create a mapping from each of the deformed frames (poses, in the Pixar paper) back to the base-pose to which the 3D texture corresponds. These reverse-mappings are encoded as a sequence of 3D textures in which each voxel encodes the position from which it originated within the undeformed volume. The quality of this 4D dataset can then be traded off against its memory footprint by altering its resolution in any of the 4 dimensions (that is, spatial or temporal).

At render-time any point in space within the bounds of the volume encoded by the dataset (points outside this region are assumed to be static) can be looked up within the 4D dataset to establish the point within the undeformed volume from which it originated.

In a variant of the present embodiment, as many selection textures are created and stored as there are models (one for each of the n defined animation frames). Selection textures are created from the master model in a process similar to the creation of the plurality of heart models. This requires more memory, but can provide more accurate results.

The process of generating the simulated ultrasound image will now be described in more detail.

Figure 10:
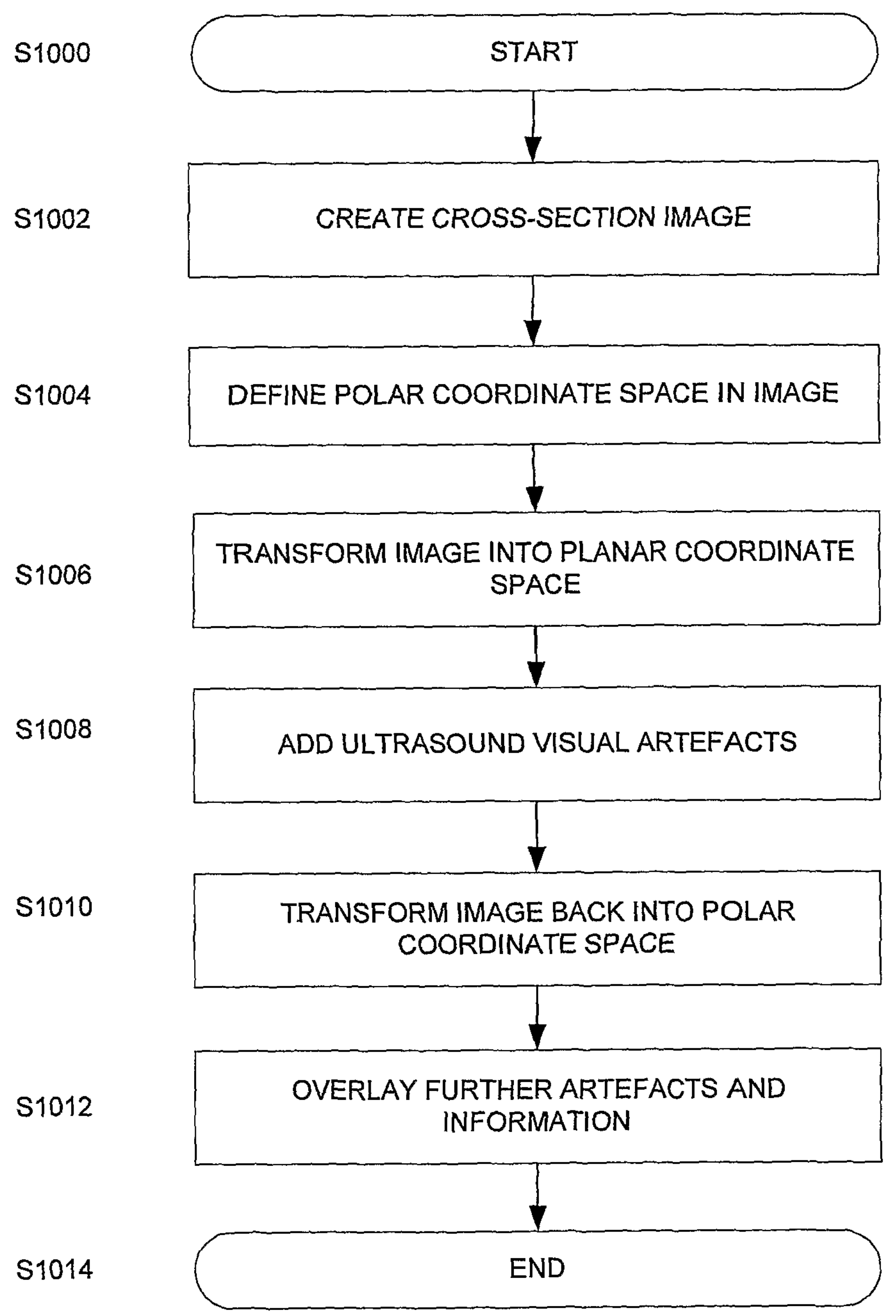
FIG. 10 is a flow chart illustrating the process steps to form the ultrasound image of FIGS. 7 and 8.

FIG. 10 is a flow chart illustrating the process steps to form the ultrasound image of FIGS. 7 and 8.

The process begins at step S1000. After the cross-section image is rendered in step S1002 as described above, a polar coordinate system is applied to the image (step S1004). Also as described above with reference to FIG. 3, the polar coordinate system has its origin at the 'apex' of the ultrasound image. The radial direction of the polar coordinate system extends out in the direction of the ultrasound probe signals. The image is then 'unwrapped' in step S1006 into a planar coordinate system. Thus the cone-shaped image is converted into a rectilinear image. This means that each column of the planar image corresponds to the path of a probe signal, simplifying the subsequent computations. In step S1008, a number of ultrasound artefacts are added to the image, as is described in more detail below. Then the image is converted back into the polar coordinate space (in step S1010), and some further artefacts and information are overlaid (step S1012). The conversion of the image into polar coordinate space and back again also helps to simulate the degradation in resolution further away from the ultrasound transducer. The process then ends in step S1014.

The process of adding ultrasound artefacts is described in more detail with reference to FIG. 11.

Figure 11:
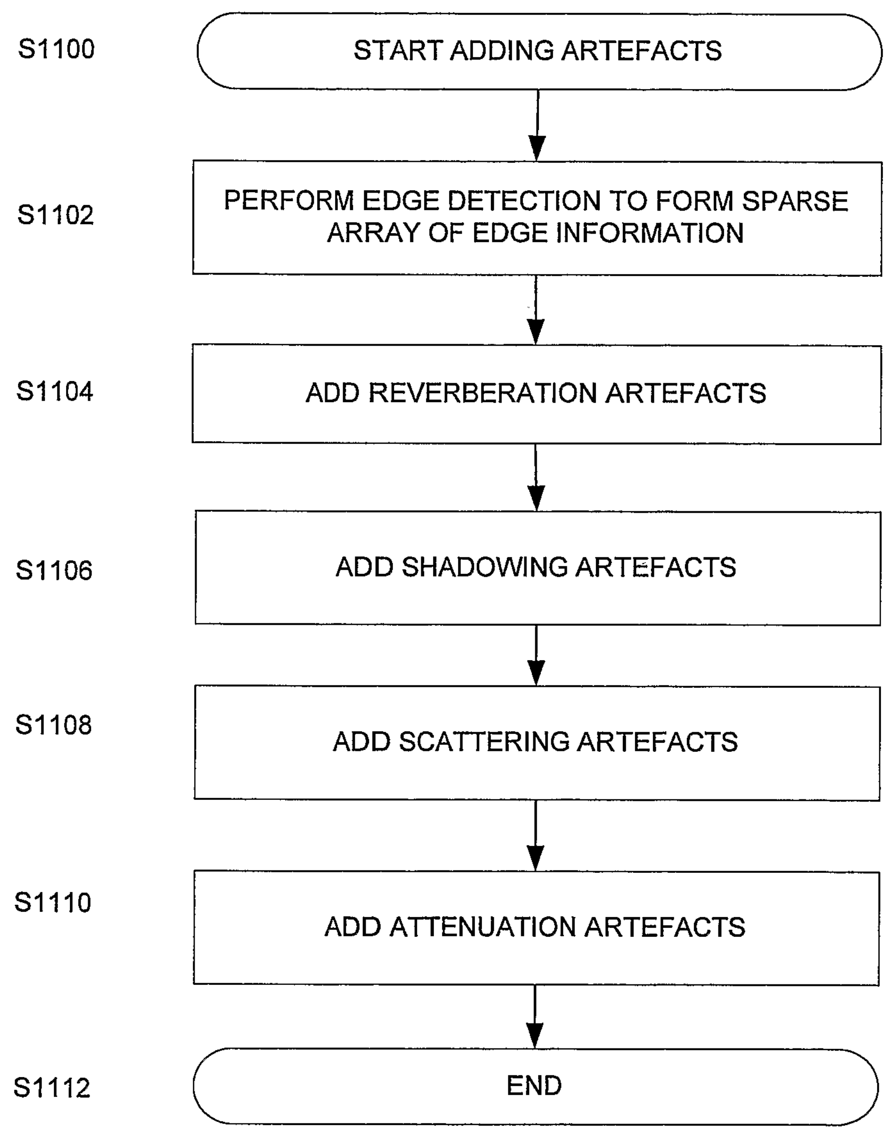
FIG. 11 is a flow chart illustrating in more detail the process step of adding ultrasound artefacts of FIG. 10.

FIG. 11 is a flow chart illustrating in more detail the process step of adding ultrasound artefacts (step S1008) of FIG. 10.

After the process begins (step S1100), an edge detection algorithm is run on the 'unwrapped' ultrasound image (step S1102), generating a sparse array including the edge transitions for each column of the image. The edge detection data is then used to add reverberation artefacts (step S1104), shadowing artefacts (step S1106) and scattering artefacts (step S1108), all of which artefacts arise from underyling physical effects relating to the ultrasound waves. Additional artefacts simulating attentuation effects are also added in step S1110. The process then ends (step S1112).

In more detail, the reverberation effects mirror the effect of multiple reflections between edge transitions in the imaged tissue, creating 'ghost' images. To keep the algorithm computationally efficient, a limit is placed on the number of reflections that are traced. The shadowing artefacts involve attenuating the image behind sharp edge transitions, mirroring the real physical effects. The scattering artefacts relate to the scattering of ultrasound sound waves, and are implemented by adding local gaussian noise in the vicinity of sharp edge transitions.

The physical effects relating to ultrasound can also be computed, for example, by calculating the amplitude and phase of sound during propagation and reflection, and summing the direct sound and all reflected sounds in order to obtain the sound level pressure level distribution around the heart. Further examples of modelling reflections and shadowing include ray-tracing, cone-tracing, and pyramid tracing models.

Figure 12:
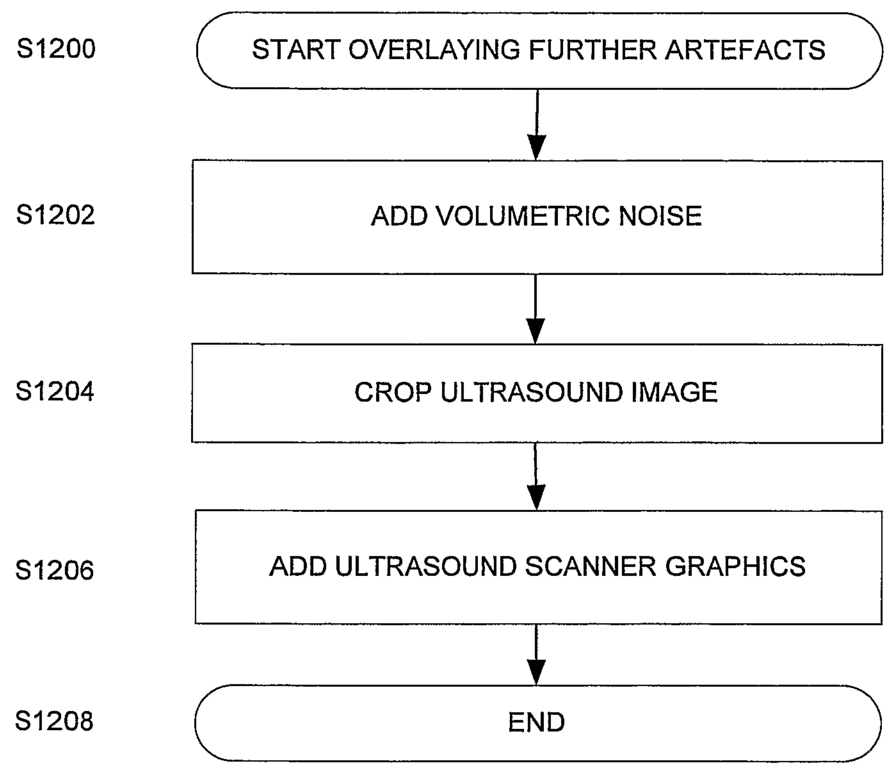
FIG. 12 is a flow chart illustrating in more detail the process step of overlaying further artefacts and information of FIG. 10.

FIG. 12 is a flow chart illustrating in more detail the process step of overlaying further artefacts and information (step S1012) of FIG. 10.

After the process begins (step S1200), volumetric noise is added (step S1202) to simulate the effect of random tissue density variations. A master volumetric noise texture is created using a guassian noise algorithm, and is deformed for each of the animation frames (and 'inbetween' frames). Relevant portions of the volumetric texture are selected and overlaid on the image data. This provides a consistent noise texture in the ultrasound images that is consistent and repeatable as the viewing angles change. In step S1204 the image is cropped into the 'cone' ultrasound shape, and in step S1206 some basic graphics (dotted lines at the edge of the scan and some information text) are added to simulate the output of the simulated ultrasound imager. The process then ends (step S1208).

Some form of sharpening can also be applied to the image to enhance the edge effects.

Figure 13:
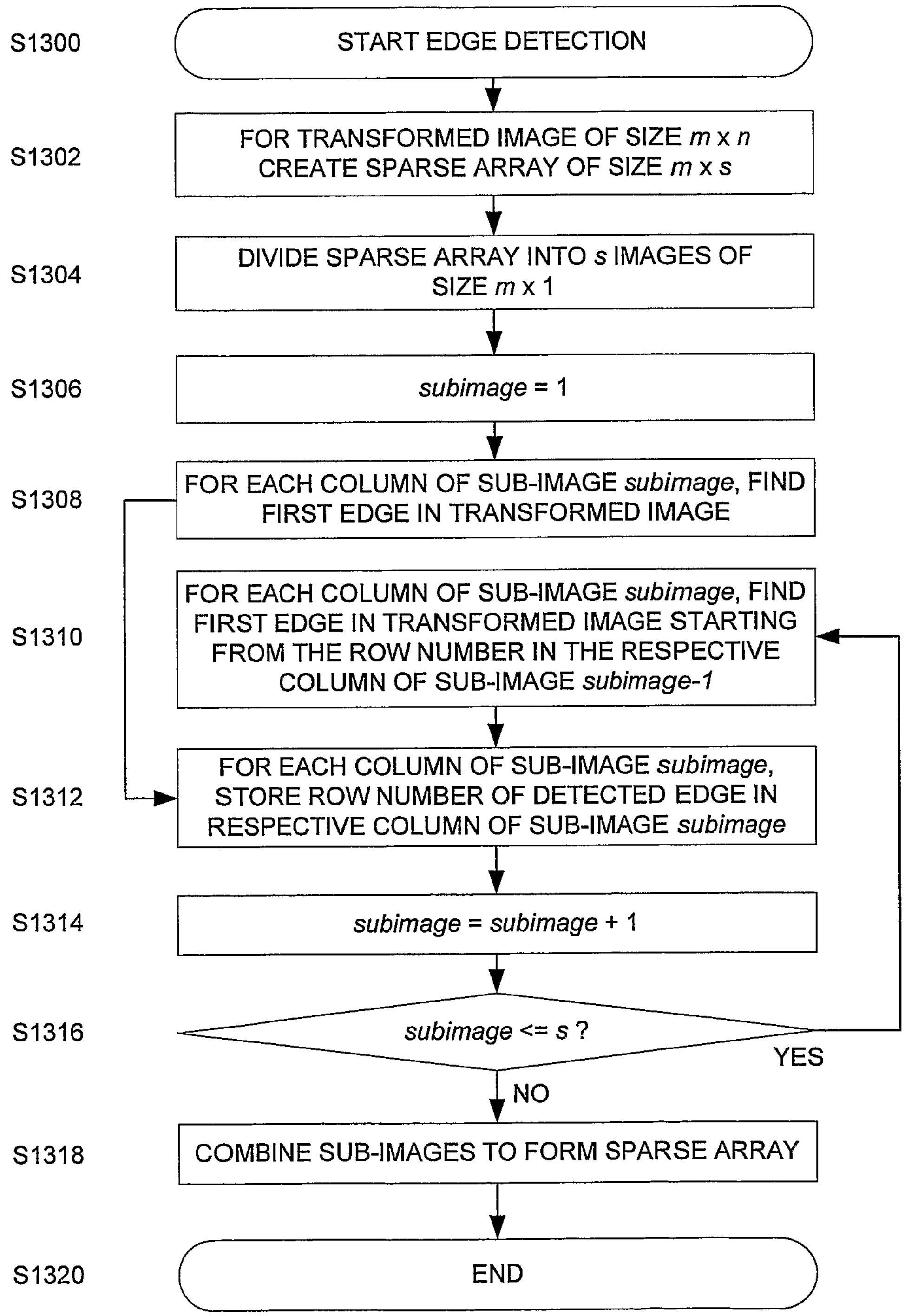
FIG. 13 is an overview of the process steps of FIGS. 10, 11 and 12.

FIG. 13 is a flow chart illustrating in more detail the process step of detecting edges (step S1102) of FIG. 11.

After the process begins (step S1300), a sparse array of size m×s is generated (or rather, reused) in step S1302. For reasons that are explained below, the sparse array takes the form of an image, in which the colour values at each pixel in fact encode data, specifically the row numbers of consecutive detected edges. In more detail, edge detection is performed on the output image by scanning down each column of the image. Each consecutive edge found in each column is stored in the next available row in the respective column of the sparse array. Thus (and significantly, in terms of the processing arrangements) the data values in each column of the sparse array are independent of the data values in other columns (but the rows in each column are inter-dependent, because the value for each row depends on the number of edges previously detected). An appropriate value for s is chosen to give accurate processing in the majority of cases, but while keeping memory use to a minimum. Therefore, at most, a total of s edge transitions can be recorded.

In step S1304 the array is divided into a total of s sub-images, each of size m×1. This is done to take advantage of the fact that the edge detection values of each column of the sparse array are independent. By turning the array into sub-images, the array can then be processed by the GPU, which employs a substantial amount of parallel processing. The images need to be broken up by row because of the inter-dependency of consecutive rows (which prevents the GPU's parallel processing being applied to the array as a whole). Steps S1306 to S1316 represent a loop in which all of the rows (and corresponding sub-images) are processed in turn. At the start of the loop, the subimage counter is set to 1 (step S1306) and the first row of the sparse array (sub image number 1) is filled with the row numbers in the transformed image that correspond to the first detected edges (step S1308). On other iterations of the loop, the previous row numbers are loaded from the previous sub-image (that is, the previous row of the sparse array), and edges are detected from that point onwards (step S1310), reducing the volume of calculations that are required. The next rows that are determined are then stored in the relevant columns of the sparse array (step S1312). The row pointer (sub-image number) is incremented (step S1314) and the loop iterates (step S1316) if more rows remain. The sub-images are then recombined in the appropriate order to form the sparse array of detected edges. The process then ends (step S1320).

If the last edge in the image has been detected, a special 'flag' value is set in the relevant column of the sparse array.

The process by which edges are detected can either involve using conventional image edge detection algorithms on the transformed image itself (for increased computational efficiency), or by mapping points on the transformed image back to the model, and using conventional ray tracing algorithms to detect surface crossings in the model (for increased accuracy, and also to allow more information to be imported regarding the nature of the edge transitions).

As described above, the information in the sparse array can be used to provide computationally efficient reverberation, shadowing, scattering and other visual artefacts (since these artefacts are typically associated with edge transitions).

Figure 14:
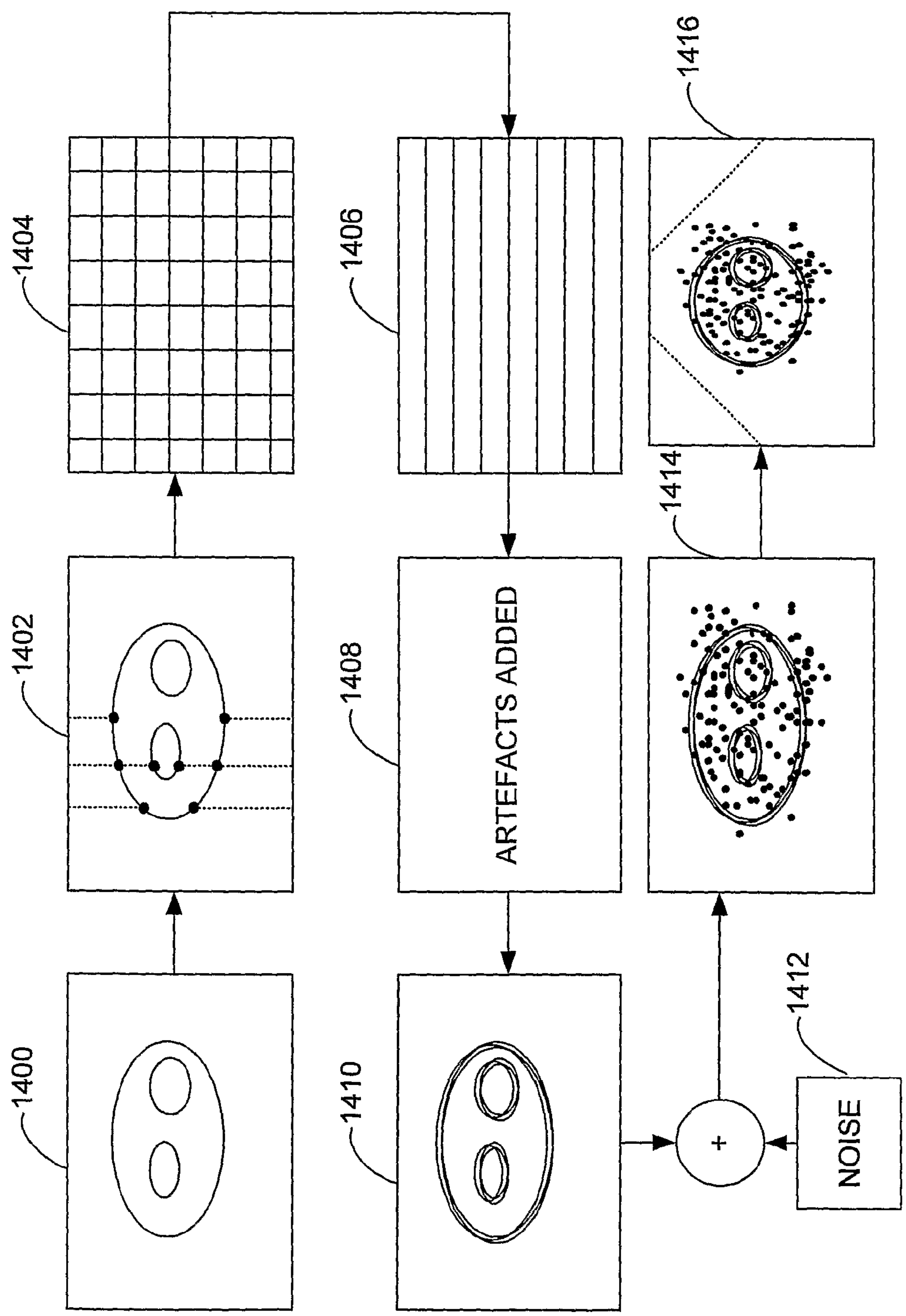
FIG. 14 is an overview of the process steps of FIGS. 10 to 13.

FIG. 14 is an overview of the process steps of FIGS. 10 to 13.

Image 1400 is an illustration of a cross-section image that has been transformed from a polar coordinate space into a planar coordinate space. Image 1402 illustrates the process of detecting edges in image 1400. Image 1404 illustrates the sparse array used to hold the edge detection information. Image 1406 illustrates how the sparse array is divided into a plurality of sub-images (running from top to bottom of the image). Step 1408 illustrates the addition of visual artefacts to the transformed image 1400 (using the sparse array) Image 1410 illustrates schematically the effect of adding various visual artefacts. Gaussian noise 1412 is then added to simulate the effects of scattering, to form the image 1414. The image 1414 is then converted back into the planar coordinate space, and the further information is overlaid to form image 1416.

A further embodiment will now be described with reference to FIGS. 15 to 19, in which a more comprehensive ultrasound simulator is provided for TOE ultrasound training.

Figure 15:
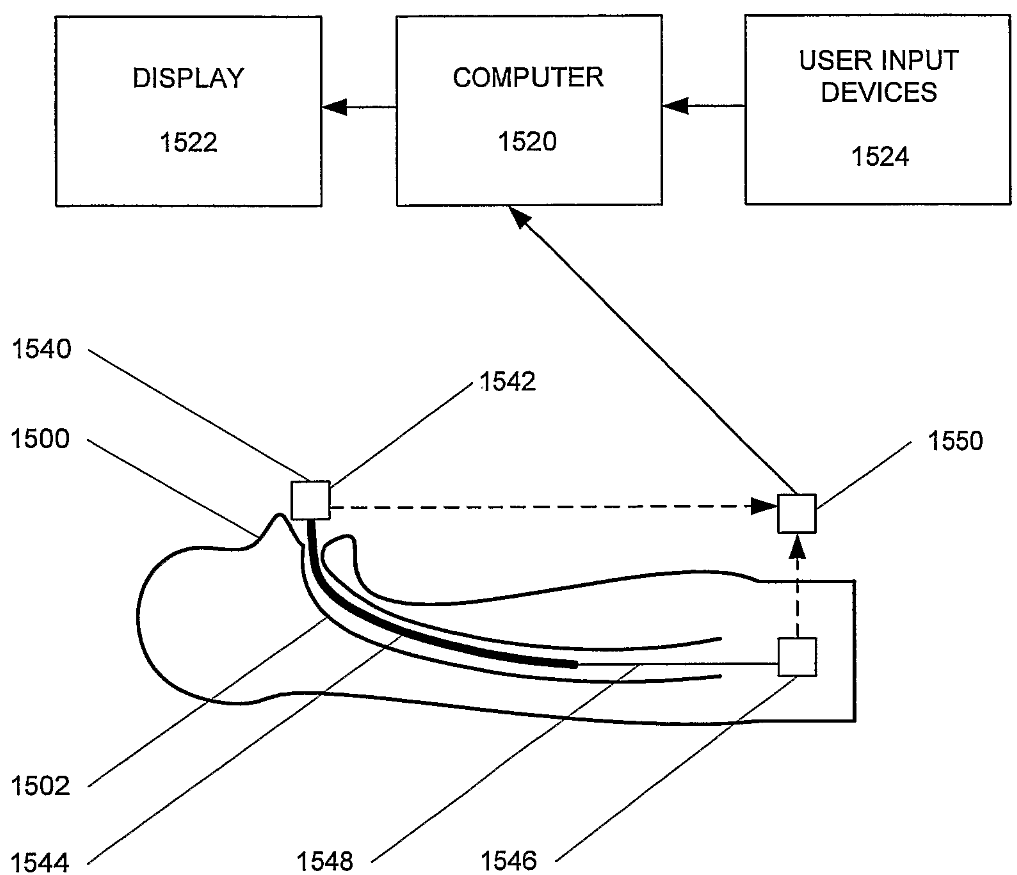
FIG. 15 is an illustration of an ultrasound simulation system in accordance with a further embodiment.

FIG. 15 is an illustration of an ultrasound simulation system in accordance with a further embodiment.

In FIG. 15 a mannequin 1500, computer 1520 and simulator probe 1540 are shown.

The mannequin is a human-like torso including a channel 1502 for receive the probe 1540 in an oesophagus-like cavity.

The computer 1520 is attached to an output display 1522 and user input devices 1524 (such as a keyboard and mouse). The computer 1520 is operable to run the ultrasound simulation system of the first embodiment, with some additional functionality as described below.

The simulator probe 1540 includes a handle and control unit 1542 designed to be similar or identical to real transoesophageal ultrasound probes, and a probe body 1544 for insertion into the oesophageal channel 1502. The probe is connected to a sprung reel 1546 by a string 1548. Both the handle and control unit 1542 and the sprung reel 1546 output data to the probe control unit 1550, which monitors the data output by the handle and control unit 1542 and reel 1546 and converts them into data representing the position of the tip of the probe within the mannequin. This positional data is then transmitted to the computer 1520. (In an alternative embodiment the raw data is transmitted to the computer 1520, and the relevant positional calculations are carried out on the computer.)

The probe has a flexible tubular structure emulating a realistic representation of a medical probe commonly used in TOE procedures.

A conventional USB interface is used to transmit the data from the unit 1550 to the computer 1520, but other interfaces and data protocols can of course be used.

In more detail, the probe handle contains a set of accelerometers which are used to deduce the orientation of the probe, and the reel tracks the length of string which has been extended out to the probe tip (from this, the distance traveled by the probe inside the mannequin can be deduced). An accelerometer such as the MMA7260QT low cost capacitive micromachined accelerometer from Freescale Semiconductor was found to be adequate for this purpose.

Figure 16:
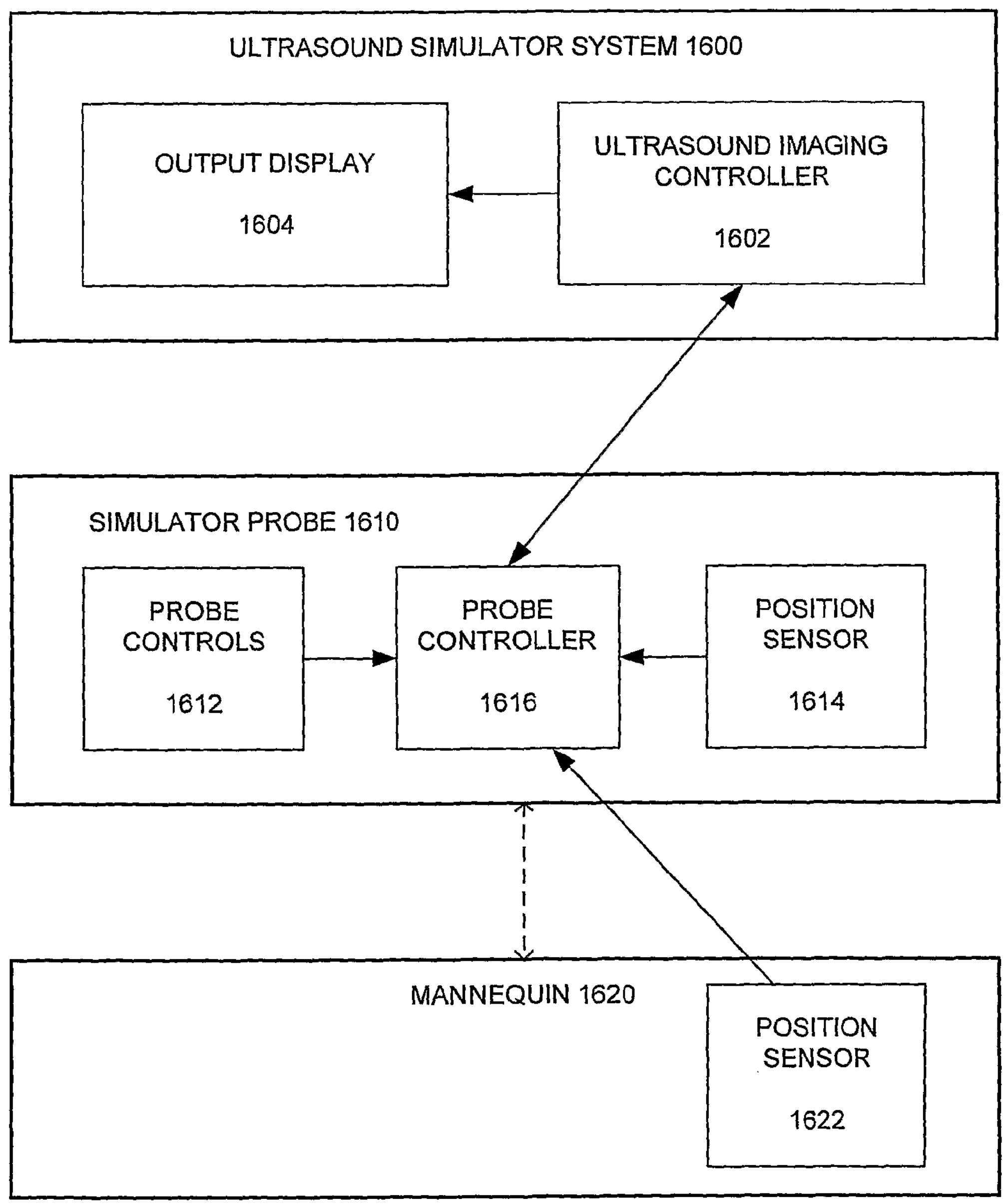
FIG. 16 is a schematic of the components of the simulator system in more detail.

FIG. 16 is a schematic of the components of the simulator system in more detail.

FIG. 16 shows schematically the ultrasound simulator system 1600, the simulator probe system 1610, and the mannequin 1620.

The simulator system 1600 includes the ultrasound imaging controller 1602, as described above in relation to the first embodiment, and an output display 1604 (amongst other things). The simulator probe 1610 includes probe controls 1612 (described below), a position sensor 1614 (the accelerometers mentioned above), and a probe controller 1616. The mannequin includes a position sensor 1622 (the sprung reel).

Figure 17:
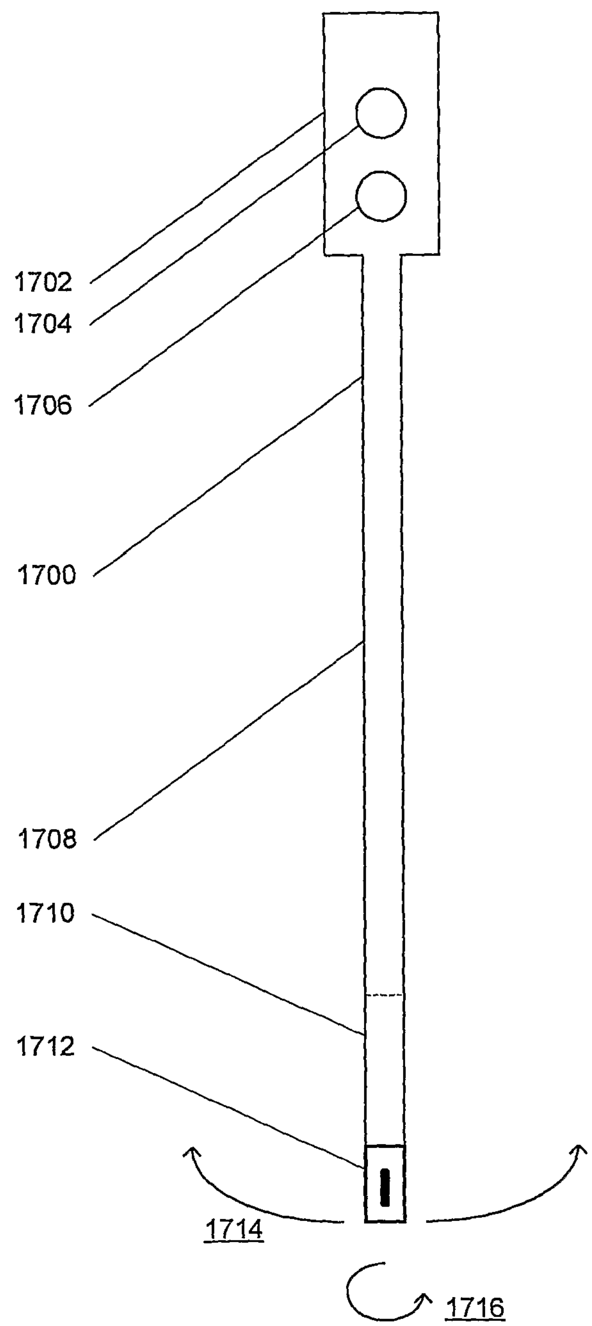
FIG. 17 illustrates the operation of a typical ultrasound transducer, illustrating the controls and movements requiring simulation.

FIG. 17 illustrates the operation of a typical ultrasound transducer, illustrating the controls and movements requiring simulation.

The probe 1700 includes a handle/control portion 1702, including user-controllable dials 1704 and 1706, a body portion 1708, a tip portion 1710, and the ultrasound transducer itself 1712.

The tip portion 1710 can be controlled by the dials 1704, 1706 to flex in a particular direction. In one example probe, the dial 1704 causes lateral (side to side) flexion as indicated by the arrows 1714, and the other dial 1706 causes antero-posterior (forward and backwards) flexion, in and out of the plane of the figure. In practice, only the antero-posterior flex dial is used, because other angles can be achieved by simple rotation of the entire probe 1700, as indicated by the arrow 1716.

Thus, at least the state of one user-controllable dial (replicated on the simulator probe), the orientation of the probe handle and the apparent length traveled by the probe need to be taken into account to calculate the position and orientation of the ultrasound transducer 1712. From this information, the region that would be imaged by the probe (if it were real) can be determined. This region information can then be fed into the simulator system to show the location of the probe on the three-dimension view, and the corresponding ultrasound that would be obtained (with reference to FIGS. 7 and 8).

Thus, the system shown in FIGS. 15 to 17 can provide a realtime simulated ultrasound output based on the apparent position of the simulator probe within the mannequin.

In variants of the present embodiment, different sensing schemes can be provided to determine the apparent position of the probe tip. In one variant, the oesophageal channel in the mannequin is constructed realistically, and the position of the probe tip is determined by magnetic or radio-frequency triangulation or the like, using a sensor and/or transmitter on the probe where the transducer would normally be. In another variant, the probe tip is magnetised, and the position of the tip is determined by polling a plurality of hall effect sensors (or the like) disposed within the mannequin channel.

Figure 18:
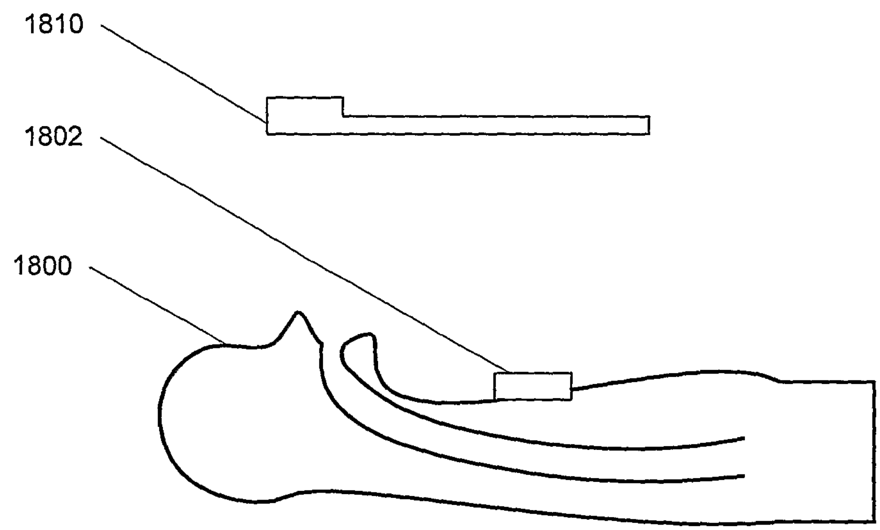
FIG. 18 is an illustration of a variant of the embodiment of FIGS. 15 to 17.

FIG. 18 is an illustration of a variant of the embodiment of FIGS. 15 to 17.

In FIG. 18, a mannequin 1800 and a free-ranging probe 1810 are shown.

In this variant, the accelerometer in the probe handle is used to track the location and orientation of the probe, and from this the position of the tip of the probe is inferred, based on the fact that the constraints of the channel within the mannequin and the resilience of the probe body can allow the position of the probe tip to be calculated for a range of placements of the probe. A further computation is required in order to calculate the relative position of the probe and the mannequin.

In order to allow this, there is a calibration mode, in which the probe is positioned in a known orientation in a known location, indicated on the mannequin by an appropriate marking or engaging module 1802. Using the calibration location and orientation as a reference, the relative position and orientation of the probe can then be determined. From time to time the probe may need to be recalibrated on account of long-term drift in the positions computed by the accelerometer.

Similar principles may also be used in triangulation or other sensing schemes. In addition, a model can be stored in the computer that defines the shape of the mannequin and the channel, in order to assist with the computation of the probe tip.

Figure 19:
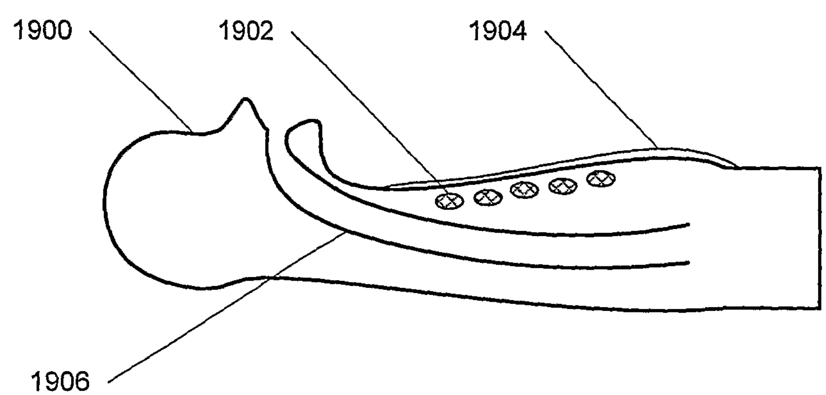
FIG. 19 is an illustration of a further variant of the embodiment of FIGS. 15 to 17.

FIG. 19 is an illustration of a further variant of the embodiment of FIGS. 15 to 17.

In this variant, the mannequin 1900 is provided with rib-like structures 1902 and a deformable outer layer 1904 resembling the consistency of a skin layer. This mannequin is adapted to allow the simulation of transthoracic ultrasound, or other external ultrasound techniques. Some form of probe or simulated transducer (not shown) can be used as before, using any of the appropriate positioning techniques described above to track its position, and using the simulator computer system to display the results of the ultrasound simulation in real-time.

The provision of the rib-like features 1902 and the deformable outer layer 1904 replicate with greater accuracy the effect of carrying out a transthoracic ultrasound examination, and can thus improve the accuracy of the simulation.

The channel 1906 can be provided as before, for increased flexibility in the simulation, but is not essential.

Some further embodiments and variations of the above embodiments will now be described.

In one embodiment, various aspects of the model are parameterised. That is to say, aspects of the model can be modified in various ways by variable amounts. For example, one parameter may be an overall scaling factor to be applied to the model geometry. Another parameter could be a scaling factor to be applied in one dimension only. Other parameters could relate, for example, to the scaling of individual components of the model. In variants of the embodiment, parameters relate also to timings relating to the model, for example to define the relative length of some parts of the cycle relative to others, and the like.

The parameters are given effect during the rendering of the model data by applying transformations to the model in real-time. Alternatively the parameters can be taken into account during the rendering of the animation frame models from the master model.

The use of parameters can effectively allow entirely new models to be created by specifying only a few pieces of data.

This can also allow various pathologies and deformities to be characterised in medically meaningful ways. In addition, parameter sets can be created or generated as a training aid.

Figure 20:
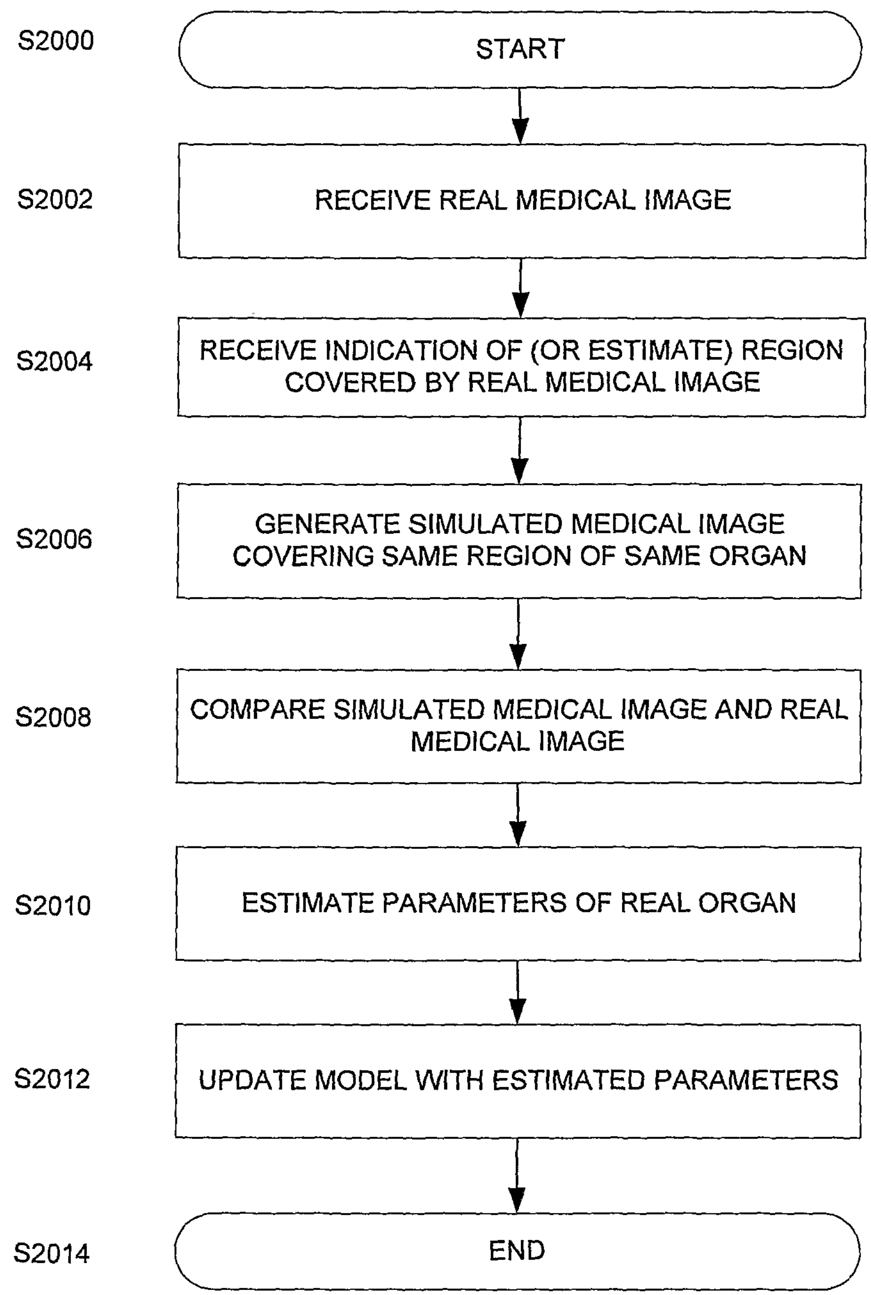
FIG. 20 is an illustration of a further embodiment involving parameterisation.

FIG. 20 is an illustration of a further embodiment involving parameterisation of the anatomical model.

In this embodiment, real medical data is analysed to infer parameters that would deform the simulated model to correspond to the real imaged anatomical structure.

After the process begins (step S2000), a real medical image is received (step S2002), for example as the output of a real ultrasound scanner. An indication is received (step S2004), for example from the scanner device, or else estimated (by eye or by statistical analysis of the medical image and comparing with the stored model), of the region that has been imaged by the scanner. Next (step S2006), a simulated image is generated based on the determined (or estimated) region. The simulated and real images are then compared (step S2008) to analyse significant differences between the two. Statistical analysis is then undertaken (or an assessment by eye, if preferred) in step S2010 in order to estimate relevant parameters of the real imaged organ (in order to estimate time-based parameters a series of images may be compared). These parameters are then stored and applied to the simulator model (step S2012). The process then ends (step S2014).

The parameters thus estimated can then be used to investigate possible pathologies involved in the imaged organs, with any information regarding deviations from the norm presented in a more useful fashion than would be apparent necessarily from the raw medical image data. The parameters can be uploaded via a network to a central database, for example, either to add to an existing medical record, or to allow a remote diagnosis to be undertaken, for example.

In a variant, the steps S2006 and S2008 can be omitted, and a statistical analysis carried out solely on the supplied real medical image (making reference to the model data where necessary). A Bayesian analysis, for example, while computationally demanding, can lead to reasonable estimates of parameters when all of the known information (from the standard model and knowledge of ultrasound artefacts, for example) is taken into account.

In another embodiment, the simulator system can be used to simulate the implantation of a medical device such as a stent or a pacemaker. The implantation of these devices is performed under local anesthesia in a hospital by a surgeon assisted by a cardiologist. These devices are positioned on the areas of the heart that require stimulation. Therefore, training can be essential for medical students to experience and visualise the appropriate positioning of these devices.

The implanted medical device can be modelled, with model data being made available as per the heart model described above, for example (albeit omitted the animation information and multiple models, because they are not needed). The position of the medical device can be altered, either via user input via a keyboard and mouse or similar, or by a simulation similar to that described above in relation to the ultrasound probe. The medical device can then be displayed in a similar way to the above-mentioned heart model, by being shown both in a three-dimensional rendering and also in a two-dimensional imaging simulation.

In a further embodiment, the model data can be used not only to provide a simulated image output, but also to create a physical model of the heart (or other modelled organ or structure), by outputting data for driving a prototyping printer (or similar device). Prototyping printers can construct an effectively arbitrary three-dimensional structure by building up consecutive 2D slices.

Thus models can be created for training purposes, or to assist in the diagnosis of pathologies (if the model is parameterised as described above, for example). This provides more flexibility than existing medical models, because the accuracy can be controlled quite tightly, and a print can be made of the heart at an arbitrary point in the cardiac cycle. In addition, because of the facility to selectively hide parts of the model, a wider range of physical models can be outputted.

The above methods and apparatuses have been described principally in relation to transoesophageal echocardiography, but it will be appreciated that these methods and apparatuses can be adapted where appropriate for use with other forms of ultrasound inspection (including transthoracic echocardiograms).

It will also be appreciated that the imaging of alternative or additional anatomical components can be simulated. For example, the heart model can be replaced or supplemented as necessary with models of lungs, stomach, liver, kidneys, and so on. Other specific structures than can be imaged/simulated include the nasopharynx, oropharynx, larynx and tracheobronchial tree with surrounding head and neck structures (with potential simulation of nasendoscopy and fibreoptic intubation). The present methods and apparatuses can also be applied to develop an epicardial echocardiagraphy simulator (this is currently carried out in the operating theatre by the surgeon, who holds the ultrasound probe directly in contact with the heart).

Another application is providing training in relation to carrying out foetal ultrasound examinations; it will be appreciated that the methods presented above for providing a plurality of models relating to different animation frames can also be used to provide multiple models representing different stages of foetal development and the like, for example. The methods and apparatuses described herein can also be applied to non-human simulations, in relation to mammals and other animals, and also to certain industrial situations (such as non-destructive testing and the examination of materials for cracks and the like) where training may otherwise be hazardous.

The medical imaging device may also be other than an ultrasound transducer. For example, it may be any one of an x-ray apparatus, a magnetic resonance imaging apparatus, and a positron-emission tomography device, for example. The artefact generation methods illustrated in FIGS. 10 to 12 can be altered as appropriate to deal with different imaging technologies.

It will further be appreciated that the image processing methods described above can also be applied to more general imaging devices (not just in the medical sphere). For example, imaging methods involving radial scanning (such as radar) may be well suited to some aspects of the artefact processing described in relation to FIGS. 10 to 12, and the simulation system can as a whole be adapted where appropriate for such scenarios.

It should also be noted that many of the systems described above, for example the generation of models, volumetric textures and the like from a master model, are provided for reasons of computational efficiency. Certainly it is possible, with increased processing power, to simplify many of these processes. For example, the master model could be rendered and processed directly when displaying the model, forming cross-sections to create the simulated output image, and so on.

Various embodiments and variants have been described above. However, it is not intended that the invention be limited to these embodiments. Further modifications lying within the spirit and scope of the present invention will be apparent to a skilled person in the art. The features of the above described arrangements may be combined in various ways to provide similar advantages in alternative arrangements.

What is claimed is:

1. A method of generating an image to simulate the output of an imaging device, the imaging device being operable to carry out a radial scan, and the method comprising:

receiving an image representing an approximation of the output of the imaging device;

defining a polar coordinate space in relation to said image, the polar coordinate space corresponding to a region swept by the radial scan;

transforming said image from the defined polar coordinate space into a planar coordinate space to form a planar-coordinate transformed image, the planar coordinate space having two orthogonal axes, one of said axes corresponding to the radial direction of the radial scan and the other of said axes corresponding to the sweep direction of the radial scan;

generating at least one visual artefact and adding said at least one visual artefact to said output image, including the step of processing at least one of individual rows and individual columns of said planar-coordinate transformed image in order to add visual artefacts to said planar-coordinate transformed image; and transforming said planar-coordinate transformed Image back into the polar coordinate space to form output image data.

2. A method according to claim 1, further comprising generating edge detection data, the edge detection data encoding information about edge transitions in the output image data.

3. A method according to claim 2, wherein the step of generating said at least one visual artefact includes processing the edge detection data to add reverberation artefacts to the output image data, the reverberation artefacts representing ghost images caused from reflections of a probe signal at a number of the edge transitions.

4. A method according to claim 2, wherein the step of generating said at least one visual artefact includes processing the edge detection data to add shadow artefacts to the output image data, the shadow artefacts representing a masking of certain portions of the imaged region caused by the attenuation of a probe signal at a number of edge transitions.

5. A method according to claim 2, wherein the step of generating said at least one visual artefact includes adding systematic artefacts to the planar-coordinate transformed image, the systematic artefacts having characteristics varying in dependence on one of the axes of the planar coordinate space.

6. A method according to claim 2, wherein:

the output image data includes a plurality of columns of image elements; and the step of generating the edge detection data comprises generating a sparse array of data representing the location of edge transitions, the sparse array having a plurality of columns, corresponding to respective columns of the output image data, and a plurality of rows, the value of each consecutive row of a particular column representing the location of each consecutive edge transition in the respective column of the output image data.

7. A method according to claim 6, wherein the step of generating a sparse array of data comprises:

creating a plurality of data vectors, each data vector corresponding to a row of the sparse array;

processing each of the data vectors in sequence, the processing of each consecutive data vector accessing data in the respective preceding data vector; and combining the plurality of data vectors to form the sparse array of data.

8. A method of facilitating training in relation to a medical imaging device for imaging a patient, comprising:

providing a mannequin simulating the patient;

providing a simulator probe for simulating a probe of the medical imaging device; and carrying out a method as defined in claim 1.

9. A computer comprising:

an instruction memory storing processor implementable instructions; and a processor operable to process data in accordance with instructions stored in the instruction memory;

wherein the instructions stored in the instruction memory comprise instructions for controlling the processor to perform a method as defined in claim 1.

10. A computer according to claim 9, further comprising a graphics processor unit, GPU, operable to process selection data and model data.

11. A data storage device storing computer readable code for controlling a computer to carry out the method of claim 1.

12. Apparatus of generating an image to simulate the output of an imaging device, the imaging device being operable to carry out a radial scan, and the apparatus comprising:

image input means for receiving an image representing an approximation of the output of the imaging device; and processing means configured to:

define a polar coordinate space in relation to said image, the polar coordinate space corresponding to a region swept by the radial scan;

transform said image from the defined polar coordinate space into a planar coordinate space to form a planar-coordinate transformed image, the planar coordinate space having two orthogonal axes, one of said axes corresponding to the radial direction of the radial scan and the other of said axes corresponding to the sweep direction of the radial scan;

generate at least one visual artefact and adding said at least one visual artefact to said output image, including the step of processing at least one of individual rows and individual columns of said planar-coordinate transformed image in order to add visual artefacts to said planar-coordinate transformed image; and transform said planar-coordinate transformed image back into the polar coordinate space to form output image data.

13. Apparatus according to claim 12, further comprising edge detection means for generating edge detection data, the edge detection data encoding information about edge transitions in the output image data.

14. Apparatus according to claim 13, wherein the processing means is further configured to process the edge detection data to add reverberation artefacts to the output image data, the reverberation artefacts representing ghost images caused from reflections of a probe signal at a number of the edge transitions.

15. Apparatus according to claim 13, wherein the processing means is further configured to process the edge detection data to add shadow artefacts to the output image data, the shadow artefacts representing a masking of certain portions of the imaged region caused by the attenuation of a probe signal at a number of edge transitions.

16. Apparatus according to claim 13, wherein the processing means is further configured to add systematic artefacts to the planar-coordinate transformed image, the systematic artefacts having characteristics varying in dependence on one of the axes of the planar coordinate space.

17. Apparatus according to claim 13, wherein:

the output image data includes a plurality of columns of image elements; and the processing means is further configured to generate a sparse array of data representing the location of edge transitions, the sparse array having a plurality of columns, corresponding to respective columns of the output image data, and a plurality of rows, the value of each consecutive row of a particular column representing the location of each consecutive edge transition in the respective column of the output image data.

18. Apparatus according to claim 17, wherein the processing means is further configured to:

create a plurality of data vectors, each data vector corresponding to a row of the sparse array;

process each of the data vectors in sequence, the processing of each consecutive data vector accessing data in the respective preceding data vector; and combine the plurality of data vectors to form the sparse array of data.

19. Apparatus for facilitating training in relation to a medical imaging device for imaging a patient, comprising:

a mannequin simulating the patient;

a simulator probe for simulating a probe of the medical imaging device; and an apparatus for generating an image as defined in claim 12.

20. Apparatus according to claim 19, wherein the mannequin includes a channel for receiving the simulator probe.

21. Apparatus according to claim 19, further comprising positioning means for determining the position of the simulator probe, the positioning means being operable to transmit positional data to the imaging apparatus.

22. Apparatus according to claim 21, wherein the positioning means includes a length measurement device for determining the length traveled by the probe within the channel.

23. Apparatus according to claim 21, wherein the positioning means includes an accelerometer mounted in the probe, for tracking at least one of the location and orientation of the probe.

24. Apparatus according to claim 21, wherein the positioning means includes at least one user-controllable input device for configuring an aspect of the probe.

25. Apparatus according to claim 21, further comprising a calibration reference location, and the positioning means being configured to transmit calibration positional data when the probe is located in the calibration reference location.

26. Apparatus according to claim 19, wherein the mannequin further comprises an internal structure simulating the rib cage of the patient.

27. Apparatus according to claim 19, wherein the mannequin further comprises a deformable outer membrane to simulate the skin layer of a patient.

* * * * *